(12) United States Patent
Callister et al.

(10) Patent No.: US 7,975,697 B2
(45) Date of Patent: Jul. 12, 2011

(54) METHODS AND APPARATUS FOR OCCLUDING REPRODUCTIVE TRACTS TO EFFECT CONTRACEPTION

(75) Inventors: Jeffrey P. Callister, Deephaven, MN (US); William S. Tremulis, Minnetrista, MN (US)

(73) Assignee: Conceptus, Inc., Mountain View, CA (US)

( * ) Notice: Subject to any disclaimer, the term of this patent is extended or adjusted under 35 U.S.C. 154(b) by 994 days.

(21) Appl. No.: 11/382,870

(22) Filed: May 11, 2006

(65) Prior Publication Data

US 2007/0261699 A1 Nov. 15, 2007

(51) Int. Cl.
*A61F 6/06* (2006.01)
(52) U.S. Cl. .................. 128/831; 128/830; 606/135
(58) Field of Classification Search .................. 128/831; 606/157, 158, 193, 135; 600/33–35, 424, 600/427; 424/422–423; 427/2.28
See application file for complete search history.

(56) References Cited

U.S. PATENT DOCUMENTS

| | | | |
|---|---|---|---|
| 3,648,683 A | | 3/1972 | Brodie |
| 3,675,639 A | | 7/1972 | Cimber |
| 3,805,767 A | | 4/1974 | Erb |
| 3,858,586 A | | 1/1975 | Lessen |
| 4,052,754 A | | 10/1977 | Pollock et al. |
| 4,606,336 A | | 8/1986 | Pavcnik et al. |
| 5,095,917 A | | 3/1992 | Vancaillie |
| 5,366,756 A | * | 11/1994 | Chesterfield et al. ........ 427/2.26 |
| 5,556,396 A | | 9/1996 | Cohen et al. |
| 5,601,600 A | | 2/1997 | Ton |
| 5,605,693 A | | 2/1997 | Seare |
| 5,935,137 A | * | 8/1999 | Saadat et al. .................. 606/135 |
| 5,954,715 A | | 9/1999 | Harrington et al. |
| 6,096,052 A | | 8/2000 | Callister et al. |
| 6,309,384 B1 | | 10/2001 | Harrington et al. |
| 6,357,443 B1 | | 3/2002 | Loy |
| 6,419,655 B1 | * | 7/2002 | Nett et al. ........................ 604/57 |
| 6,432,116 B1 | | 8/2002 | Callister et al. |

(Continued)

FOREIGN PATENT DOCUMENTS

WO    WO-9525490    9/1995

(Continued)

OTHER PUBLICATIONS

PCT International Preliminary Report on Patentability and Written Opinion for International Application No. PCT/US2006/022571, mailed Nov. 11, 2008, 6 pages.

(Continued)

*Primary Examiner* — Patricia M Bianco
*Assistant Examiner* — Camtu T Nguyen
(74) *Attorney, Agent, or Firm* — Blakely, Sokoloff, Taylor & Zafman LLP

(57) ABSTRACT

Systems and methods of visibly marking a reproductive tract, e.g., at least one ostium of the Fallopian tubes accessed transvaginally and transcervically, to indicate delivery of an occlusion device into the corresponding at least one Fallopian tube to effect contraception are disclosed. Marking is effected by delivery of a dye that stains the ostium and/or extension of the marking member from the delivered occlusion device into view in the uterine cavity or ostium. A catheter (or catheters) preferably introduced through a hysteroscope that illuminates and provides visualization of the uterine cavity and the ostia of the Fallopian tubes is employed to insert each contracted, stent-like, occluding device into each Fallopian tube and to mechanically expand or release to self-expand the occluding device.

30 Claims, 14 Drawing Sheets

U.S. PATENT DOCUMENTS

| | | | |
|---|---|---|---|
| 6,527,765 B2 * | 3/2003 | Kelman et al. | 606/22 |
| 6,684,884 B2 * | 2/2004 | Nikolchev et al. | 128/830 |
| 6,709,667 B1 | 3/2004 | Lowe et al. | |
| 6,726,682 B2 | 4/2004 | Harrington et al. | |
| 6,763,833 B1 | 7/2004 | Khera et al. | |
| 6,780,182 B2 | 8/2004 | Bowman et al. | |
| 7,329,414 B2 | 2/2008 | Fisher et al. | |
| 2001/0041900 A1 | 11/2001 | Callister et al. | |
| 2003/0066533 A1 | 4/2003 | Loy | |
| 2004/0079377 A1 | 4/2004 | Nikolchev et al. | |
| 2005/0033281 A1 | 2/2005 | Bowman et al. | |
| 2005/0045183 A1 | 3/2005 | Callister et al. | |
| 2005/0085844 A1 | 4/2005 | Tremulis et al. | |
| 2005/0155608 A1 | 7/2005 | Pavcnik et al. | |
| 2005/0192616 A1 | 9/2005 | Callister et al. | |
| 2005/0209633 A1 | 9/2005 | Callister et al. | |
| 2005/0274384 A1 | 12/2005 | Tran et al. | |
| 2005/0288551 A1 | 12/2005 | Callister et al. | |
| 2006/0009798 A1 | 1/2006 | Callister et al. | |
| 2007/0163601 A1 | 7/2007 | Pollock et al. | |
| 2007/0227544 A1 | 10/2007 | Swann et al. | |
| 2007/0261699 A1 | 11/2007 | Callister et al. | |

FOREIGN PATENT DOCUMENTS

| | | |
|---|---|---|
| WO | WO 98/31308 A | 7/1998 |
| WO | WO 2005/006991 A2 | 1/2005 |

OTHER PUBLICATIONS

PCT International Search Report for International Application No. PCT/US2006/022571, mailed Feb. 2, 2007, 2 pages.

International Preliminary Report on Patentability, PCT/2008/074682, (Mar. 11, 2010), 13 pages.

PCT International Invitation to Pay Additional Fees, PCT/US2008/074682, (Jan. 16, 2009), 7 pages.

PCT International Preliminary Report on Patentability and Written Opinion, PCT/US2006/022571, (Nov. 11, 2008), 6 pages.

"PCT International Search Report", Pct/US2006/022571, (Feb. 2, 2007), 2 pages.

PCT International Search Report and Written Opinion, PCT/US2008/074682, (May 11, 2009), 22 pages.

Bowman, Brett S., "A New Transcervical Sterilization Procedure: Optimal Epithelial Ablation", http://www.adiana.com/products_overview.php Adiana Inc., Redwood City, CA, 1 page.

Car-Brendel, Victoria E., "A New Transcervical Sterilization Procedure 6 Month Preclinical Results", http://www.adiana.com/products_overview.php Adiana Inc., Redwood City, CA, 1 page.

Price, Thomas M., "Permanent Transcervical Sterilization: The First 500 Women Treated in a Multi-Center Trial", http://www.adiana.com/products_overview.php Adiana Inc., Redwood City, CA, 1 page.

* cited by examiner

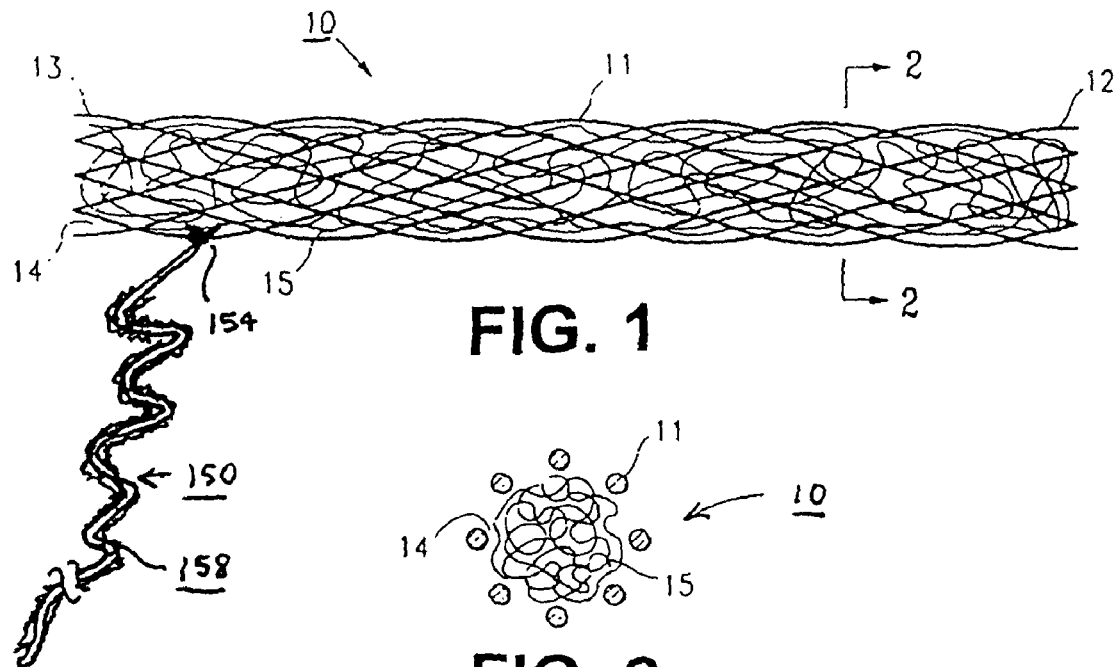
FIG. 1
FIG. 2
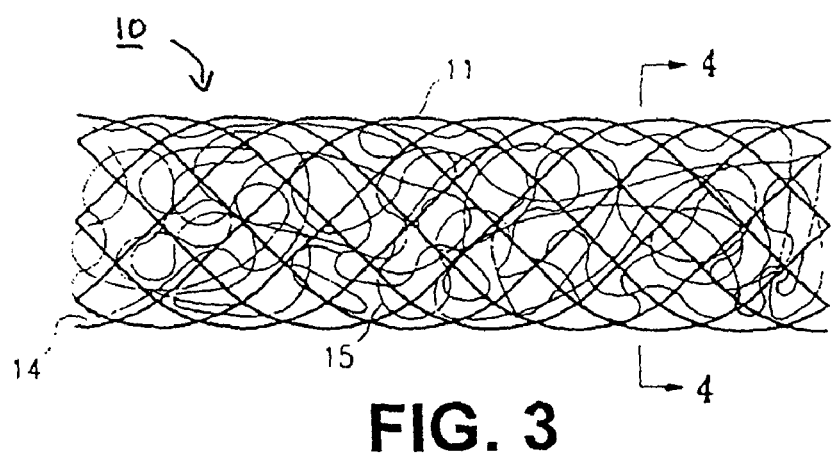
FIG. 3
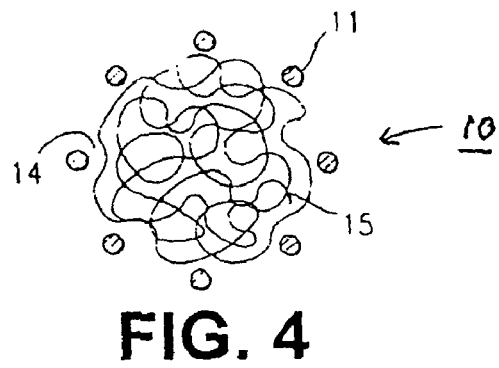
FIG. 4

METHODS AND APPARATUS FOR OCCLUDING REPRODUCTIVE TRACTS TO EFFECT CONTRACEPTION

FIELD OF THE INVENTION

The present invention pertains to effecting contraception by occluding reproductive tracts, particularly the Fallopian tubes accessed within the uterine cavity via the ostia, and particularly systems and methods of visibly marking at least one ostium of at least one Fallopian tube to indicate occlusion upon delivery of an occlusion device into the at least one Fallopian tubes.

BACKGROUND OF THE INVENTION

One form of contraception involves the occlusion of reproductive tracts, particularly, the Fallopian tubes in female subjects and the vas deferens in male subjects, with an embolic material and/or occluding device that acutely and/or chronically (following foreign body tissue reaction or epithelialization) blocks passage of sperm through the reproductive tract. Particular forms of occluding devices and systems and methods of inserting the occluding devices in the vas deferens or Fallopian tubes are described in commonly owned U.S. Pat. Nos. 6,096,052 and 6,432,116 and in commonly assigned U.S Patent Application Publication Nos. 2001/0041900, 2005/0045183, 2005/0085844, 2005/0192616, 2005/0209633, and 2006/0009798, for example, certain features of which are embodied in the Ovion™ permanent contraceptive system sold by the assignee of the present invention. Further occluding devices and systems and methods for disclosing the occluding devices in Fallopian tubes are disclosed in U.S. Pat. Nos. 6,763,833 and 6,709,667, for example.

The transvaginal and transcervical advance of the occluding device delivery catheter to dispose the occluding device in a selected Fallopian tube is aided through the use of an endoscope or hysteroscope that illuminates and provides visualization of the uterine cavity and the ostia of the Fallopian tubes. A particularly desirable flexible hysteroscope is disclosed in commonly assigned U.S Patent Application Publication Nos. 2005/0288551 that is employed to guide an occluding device installation catheter through the uterine cavity and into selected ostium of a selected Fallopian tube under such visualization.

In practice, an occluding device is assembled to the occluding device delivery catheter, and the assembly is advanced through a lumen of the hysteroscope. The hysteroscope is advanced through the transvaginal and transcervical path as the path is visualized to locate a Fallopian tube ostium and to direct the distal end of the delivery catheter into the Fallopian tube. In one approach, the occluding device is then released into the Fallopian tube by expelling the contracted occluding device from the catheter lumen, which self expands when released, enabling withdrawal of the delivery catheter. In another approach, a catheter-borne deflated balloon that the contracted occluding device is mounted to is expanded at the delivery site to thereby expand the occluding device against the Fallopian tube wall. The balloon is then deflated to enable withdrawal of the delivery catheter. The occluding device delivery process is followed to sequentially dispose one occluding device in the right Fallopian tube and another occluding device in the left Fallopian tube.

The occluding devices inserted into the Fallopian tubes employing the Ovion™ permanent contraceptive system are relatively short in length (in contrast to those disclosed in the above-referenced '833 and '677 patents) order to be as unobtrusive as possible and to avoid intruding into the uterine cavity. These occluding devices are delivered so deeply into the Fallopian tube as to be invisible from inspection of the uterine cavity employing the hysteroscope. Thus, there is no visible indication within the uterine cavity as to whether an initially installed occluding device is installed in the right or left Fallopian tube. Consequently, there is a possibility that the implanting physician may become disoriented when advancing the delivery catheter and hysteroscope within the uterine cavity and erroneously install the second occluding device into the same Fallopian tube that the first occluding device was installed into. If uncertainty arises, it may be necessary to interrupt the procedure to employ external fluoroscopy or other imaging equipment to pinpoint the location of the first installed occluding device.

Accordingly, it would be desirable to provide a way to ensure that the physician does not mistakenly install a second occluding device of the type that does not extend into the uterine cavity when installed into the same Fallopian tube that the first occluding device is installed into. It would also be desirable to mark the location of any such occluding device occluding a reproductive tract.

SUMMARY OF THE INVENTION

The preferred embodiments of the present invention incorporate a number of inventive features that address the above-described problems that may be combined as illustrated by the preferred embodiments or advantageously separately employed.

In order to eliminate any possibility of confusion, methods devices and systems are provided in accordance with the invention to visibly mark a reproductive tract that an occluding device is inserted into to occlude the tract lumen.

Methods of marking the reproductive tract include, but are not limited to: injecting a visible visualization agent or visible dye through a dye delivery lumen of the catheter to stain body tissue; providing a marking device at the catheter shaft distal end or in a catheter shaft cavity that can be deployed to apply dye to the visible tissue after the occlusion device is inserted or released and secured; applying a dye coating to the tip of the catheter that slowly dissolves on contact with body fluids to stain tissue that the catheter tip contacts when inserted into the reproductive tract to install an occluding device; or providing a marking member, e.g., a strand or filament of absorbable suture or other absorbable material, similarly dyed to be visible attached to the occlusion device so that it trails and extends from the reproductive tract after installation and may be absorbed over time. The dye of the marking member may also slowly dissolve on contact with body fluids to stain the tissue that the suture contacts.

In still further embodiments of the invention wherein the occluding device delivery catheter is adapted to be advanced over a guide member, e.g., a stylet or guide wire or the like, it is contemplated that the visible marking of the tissue may be effected by providing a dye emitting body borne on at least a segment of the guide member proximate the guide member distal end adapted to contact and visibly stain the reproductive tract as the guide member is advanced into the reproductive tract.

Preferred non-toxic dyes for staining the tissue of the ostium or for coloring bioabsorbable sutures include methylene blue dye (a benign chemical often used in conjunction with hysteroscopic fertility tests), FD&C BLUE dyes 3 and 6, eosin, and indocyanine green. Green or blue dyes are preferred as they contrast with the uterine wall tissue color. Such dyes may be delivered in liquid form from an external dye container or syringe through a dye delivery lumen of the delivery catheter and out of dye emitting ports at or near the catheter distal end.

Alternatively, the selected dye may be incorporated into a hydrophilic material in a coating surface treatment or application near the distal end of the delivery catheter or to other structures borne by the delivery catheter, wherein the dye liquefies when in contact with fluids at the tissue surface ad stains tissue walls. Alternatively, the selected dye may be incorporated into a hydrophilic material applied to a portion or the entirety of the occluding device or applied to a biodegradable suture extending from the occluding device or applied to a guidewire employed in installing the occluding device, wherein the dye liquefies when in contact with fluids at the tissue surface and stains tissue walls. For convenience, the mixture of the selected dye and hydrophilic material is referred to herein as a dye eluting or emitting body however it is applied or adhered to another structure.

In preferred embodiments of the present invention, occluding devices are inserted into the Fallopian tubes employing an occluding device delivery catheter and a hysteroscope. The tubal ostium of the Fallopian tube that at least a first occluding device is installed into is marked in one of the manners disclosed herein so that the physician can ensure that the second occluding device is inserted into the other Fallopian tube. The stain applied to the ostium tissue or the dyed suture is visible in use of the hysteroscope that the surgeon employs to view the uterine cavity and identifies the Fallopian tube to be avoided in the subsequent installation of the second occlusion device. Advantageously, the physician is visually alerted to direct the delivery catheter into the unstained, tubal ostium to deliver the second occluding device.

This summary of the invention has been presented here simply to point out some of the ways that the invention overcomes difficulties presented in the prior art and to distinguish the invention from the prior art and is not intended to operate in any manner as a limitation on the interpretation of claims that are presented initially in the patent application and that are ultimately granted.

BRIEF DESCRIPTION OF THE DRAWINGS

These and other advantages and features of the present invention will be more readily understood from the following detailed description of the preferred embodiments thereof, when considered in conjunction with the drawings, in which like reference numerals indicate identical structures throughout the several views, and wherein:

FIG. 1 is a side view of one embodiment of an exemplary occluding device that may be employed in the method and system of the present invention in a contracted configuration;

FIG. 2 is a transverse cross section view taken along lines 2-2 of the device of FIG. 1;

FIG. 3 is a side view of the exemplary occluding device of FIG. 1 in an expanded configuration;

FIG. 4 is a transverse cross section view taken along lines 4-4 of the device of FIG. 3;

Figure 5:
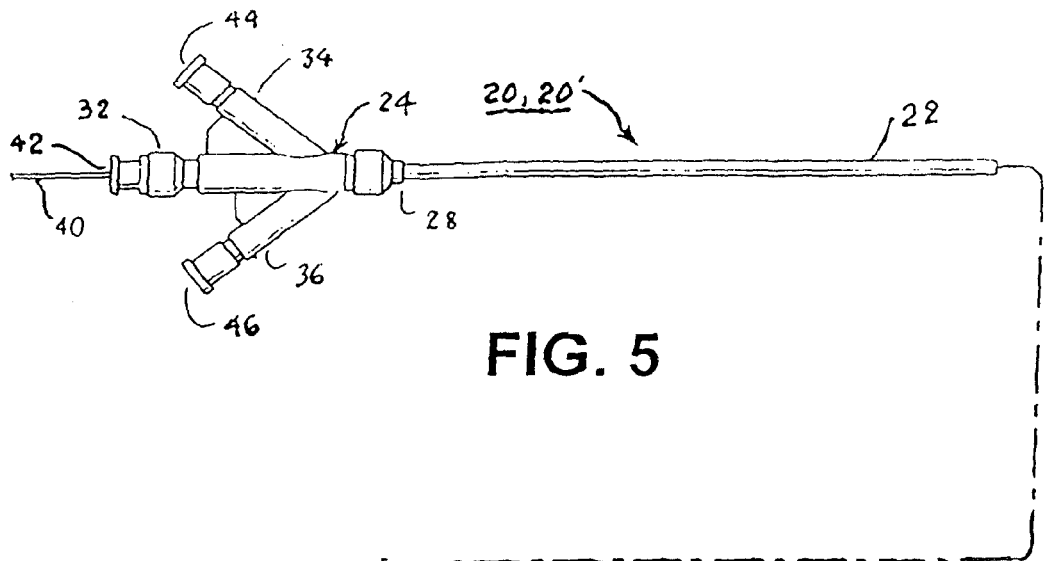
FIG. 5 is a side view in partial cross-section of the assembly of a contracted, balloon expandable, occluding device mounted upon an expandable balloon at the distal end of one embodiment of an occluding device delivery catheter adapted to mark the ostium that at least the first occluding device is installed into.

It will be understood that the drawing figures are not necessarily to scale.

DETAILED DESCRIPTION OF EXEMPLARY PREFERRED EMBODIMENTS

In the following detailed description, references are made to illustrative embodiments of methods and apparatus for carrying out the invention. It is understood that other embodiments can be utilized without departing from the scope of the invention. Preferred methods and apparatus are described for occlusion of Fallopian tubes to effect contraception.

It will be understood that the term "contraceptive device" or "occluder" or "occluding device" encompasses any type of a device adapted to be delivered into and released or otherwise installed in a reproductive tract to acutely and/or chronically occlude the reproductive tract lumen. The present invention is adaptable for use in any system or method of installing any prior art contraceptive device that occludes the Fallopian tubes of the types described above. For convenience, preferred embodiments are described hereafter in the context of the contraceptive devices and systems and methods of installing same in the Fallopian tubes disclosed in the above-referenced '116 patent modified to illustrate the present invention as described herein.

FIG. 1 from the '116 patent illustrates an occluding device 10 that can be advantageously employed in the practice of the present invention generally comprising a tubular member 11 having a first end 12, a second end 13, an occluding device lumen 14 extending therebetween, and a mesh member 15 for supporting tissue growth disposed within the occluding device lumen 14. In a presently preferred embodiment, occluding device 10 comprises a contraceptive or sterilization device for occluding a reproductive tract lumen, particularly the Fallopian tubes of a female subject.

Figure 6:
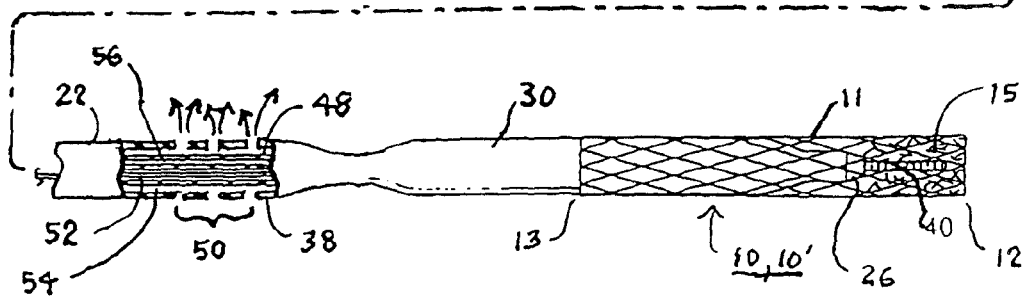
FIG. 6 is a side view in partial cross-section of the assembly of a contracted, self-expanding, occluding device mounted within a chamber at the distal end of a further embodiment of an occluding device delivery catheter adapted to mark the ostium that at least the first occluding device is installed into.
Figure 6:
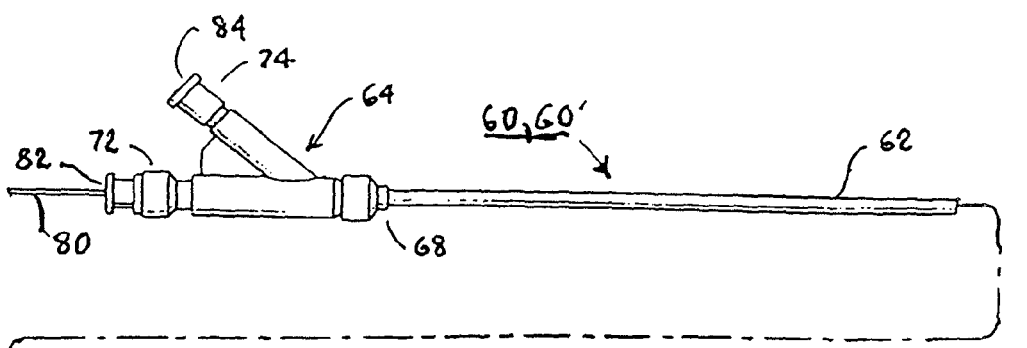
Figure 6:
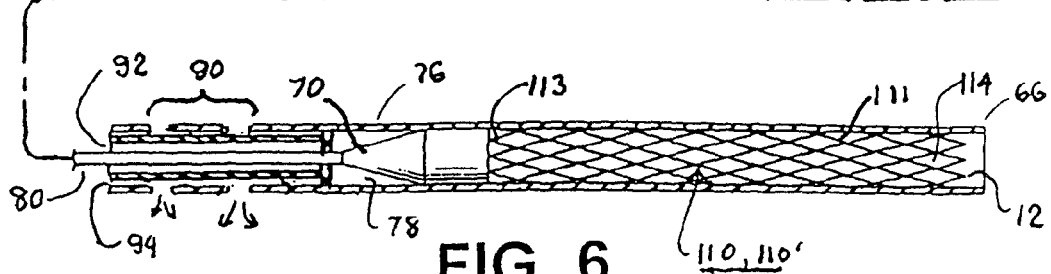

The occluding device 10 is depicted in FIGS. 1 and 2 in its relatively small diameter, contracted configuration for introduction and advancement into the Fallopian tubes. The occluding device 10 is depicted in FIGS. 3 and 4 in a relatively large dimension, expanded configuration upon installation in the Fallopian tubes. As indicated below, the expansion of the diameter of occluding balloon at the delivery catheter distal end disposed within the occluding device lumen 14 as shown in FIG. 5 or by self-expansion upon release from confinement within a device delivery lumen of the occluding member delivery catheter as shown in FIG. 6.

In the embodiment illustrated in FIGS. 1-4, a mesh member 15 extends continuously along the length of the tubular member 11 between the first or distal end 12 and a second or proximal end 13 within occluding device lumen 14, although it will be understood a shorter or a plurality of shorter sections of mesh member 15 may be disposed intermittently spaced along the length of the tubular member 15 within the occluding member lumen 14. As illustrated in FIGS. 3 and 4, the mesh member(s) 15 expands with expansion of the tubular member 11 so that mesh member(s) 15 extends across the expanded lumen 14.

In the expanded configuration depicted in FIGS. 3 and 4, the tubular member 11 has an open, lattice-type structure facilitating epithelialization or tissue ingrowth that secures the occluding device 11 to the tissue wall of the reproductive tract. Preferably, tubular member 11 can be expanded to or self-expands to an expanded diameter that is preferably equal to or slightly larger than the relaxed diameter of the reproductive tract, so that the expanded occluding device 10 is acutely secured from expulsion from the reproductive tract. For example, the expanded transverse dimension or diameter should be about 0.1 mm to about 5 mm for disposition and retention within a female patient's Fallopian tubes. The tubular member 11 may be fabricated in the fashion of a stent or in any of the ways and configurations disclosed in the above-referenced patents and publications, e.g., of the materials and employing the fabrication techniques disclosed in above-referenced U.S. Patent Application Publication No. 2001/0041900 or otherwise known in the art.

The mesh member 15 is also permeable to allow for tissue ingrowth or epithelialization, and the epithelialized mesh member 15 occludes the reproductive tract lumen sufficiently to prevent the passage of reproductive cells therethrough. For example, the mesh member 15 may comprise intertwined strands of a biocompatible material connected to the tubular member 11. In the embodiment illustrated in FIG. 1, the mesh member comprises bundled strands, but the mesh member 15 may comprise woven strands. The mesh member 15 may be connected to the tubular member 11 by a variety of suitable means including adhesive, heat bonding, or solvent bonding. A variety of materials may be used to form the mesh member 15, including plastics, polymers, metals, and treated animal tissues. For example, the mesh member 15 formed of Dacron or Nylon polymers may act as an irritant that promotes epithelialization. Additionally, the mesh member 15 may be surface coated or impregnated with epithelialization promoting agents to enhance tissue impregnation. The fibers used to form the mesh member 15 are generally about 0.00025 mm to about 0.25 mm in diameter. It would be obvious that a wide variety of mesh sizes that support epithelialization. For example, in one embodiment the mesh member 15 mesh size is about 5 µm to about 0.05 mm, and preferably about 10 µm to about 15 µm. Preferably, mesh members 15 having relatively large mesh sizes are coated with epithelialization promoting agents.

The occluding device 10 may take other forms as shown in the various embodiments of occluding devices depicted in the above-cited references or otherwise known in the art. When expanded, the occluding device 10 may have a substantially uniform transverse dimension through its length or may be tapered along its length. The occluding device 10 may be substantially shorter than as depicted, as disclosed in the above-referenced U.S. Patent Application Publication No. 2005/0045183, for example.

The occluding device 10 can be formed of and/or be coated with and/or incorporate any of the drugs or materials or mechanisms disclosed in the above-referenced U.S. Patent Application Publication No. 2006/0009798 that promote epithelialization within body tissues to create a more effective occlusion of the lumen 14 or result in a more secure attachment of the tubular member 11 to the Fallopian tube wall. For instance, polyester fibers may be attached to one or more expandable segments of the tubular member 11 to bear against the Fallopian tube wall such that tissue ingrowth into the lumen 14 occurs more rapidly. A galvanic electrical current can be generated in the tissue surrounding the occluding device 10 to stimulate epithelialization by appropriate selection of dissimilar metals for the tubular member 11 and mesh member(s) 15 as disclosed in the above-referenced U.S. Patent Application Publication No. 2005/0209633.

A slow-release contraceptive substance may also be embedded with the mesh member 15 within the lumen of the tubular member 11 that provides contraception during the time that it takes for tissue ingrowth to fully obstruct the tubular member lumen 14 as disclosed in the above-referenced U.S. Patent Application Publication Nos. 2005/0045183 and 2006/0009798, for example.

The mesh member 15 may be replaced or supplemented by permanent or biodegradable barriers that block passage of sperm or eggs through the occluding device lumen 14 either acutely or chronically. For example, such barriers may include a detachable balloon that is inflated or a foam disk or an impermeable membrane that self-expands or is expanded as the tubular member expands during installation to block passage of sperm or eggs through the tubular member lumen until tissue growth fills the occluding device lumen as disclosed in the above-referenced U.S. Patent Application Publication 2005/0192616.

Figure 14:
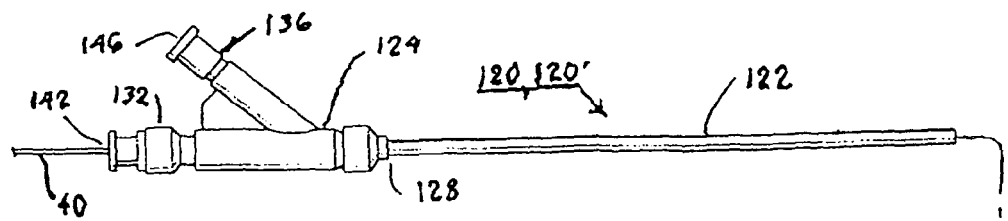
FIG. 14 is a side view in partial cross-section of the assembly of a contracted occluding device mounted upon an expandable balloon at the distal end of a further embodiment of an occluding device delivery catheter adapted to mark the ostium that at least the first occluding device is installed into with a dyed or dye emitting suture extending into the uterine cavity.
Figure 14:
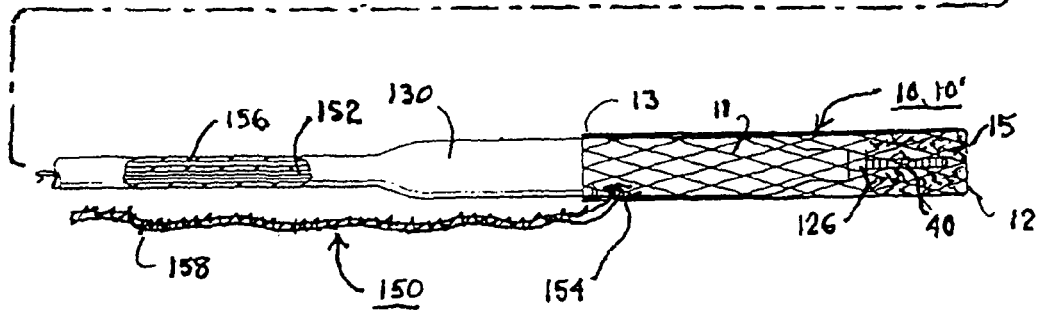
Figure 15:
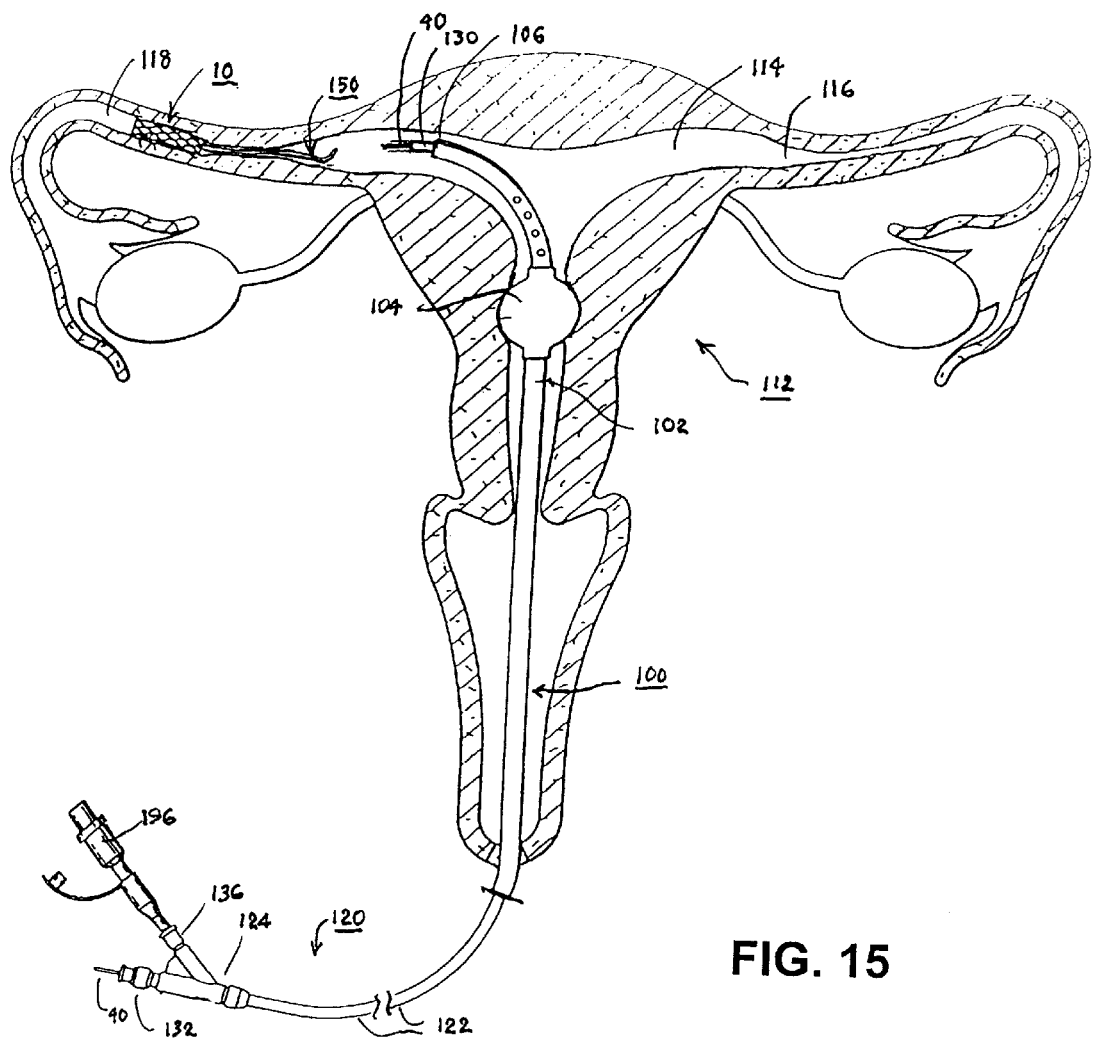
FIG. 15 is an illustration in partial cross-section depicting the viewing of the proximally stain on the ostium of the left Fallopian tube employing the hysteroscope to aid in aiming the hysteroscope distal end away from the left Fallopian tube and toward the ostium of the right Fallopian tube for installation of a second occluding device employing the delivery catheter of FIG. 5 into it.

In one embodiment of the present invention further depicted in FIGS. 14 and 15, an elongated flexible marking member or marker 150, e.g., a biodegradable suture, is attached to the occluding member 10 near the proximal end 12, e.g., by tying the distal end of the marker 150 in a knot 152 to the outer member 11. In use, the flexible marker 150 trails proximally from the installed occluding member 10 and extends into the uterine cavity to mark the Fallopian tube that the occluding member is installed in. The marker 150 is preferably colored to contrast with tissue, e.g., by being coated with a hydrophilic coating surface treatment or application that is itself visible when illuminated and viewed employing a hysteroscope and liquefies when in contact with fluids at the tissue surface to stain the tissue. For convenience, such a coated mixture of hydrophilic material with dye is referred to herein as a dye eluting or emitting body 158 in FIG. 1.

Preferred non-toxic dyes for staining the tissue of the ostium or for coloring bioabsorbable sutures include methylene blue dye (a benign chemical often used in conjunction with hysteroscopic fertility tests), FD&C BLUE dyes 3 and 6, eosin, and indocyanine green. Green or blue dyes are preferred as they contrast with the uterine wall tissue color.

In one embodiment of an occluding device delivery catheter 20 depicted in FIG. 5 for delivering an occluding device 10 not necessarily having a flexible marker 150, the occluding device 10 is expanded from a contracted outer diameter of FIGS. 1 and 2 to an expanded outer diameter of FIGS. 3 and 4 upon installation in a Fallopian tube. The occluding device delivery catheter 20 has a distal inflatable balloon 30 disposed within at least a proximal section of the occluding device lumen 14 that supports and expands the occluding device 10 in the installation procedure. In this embodiment, a short mesh member 15 and/or barrier is disposed within the occluding device lumen 14 proximate the distal end of the outer member 11 and distal to the contracted balloon 30.

The exemplary delivery catheter 20 comprises an elongated catheter shaft 22 extending between a proximal end 28 connected with a proximal hub 24 to a distal end 26 distal to the deflated balloon 30. The proximal hub 24 comprises an axially and proximally extending adapter 32 and proximally extending angled adapters 36 and 38 that have adapter lumens coupled to shaft lumens with catheter shaft 22.

The proximally extending adapter 32 encloses an adapter lumen 42 that is aligned with guidewire lumen 52 extending through the length of the shaft 22 to the shaft distal end 26. A guidewire 40 is depicted in FIG. 5 extending through the adapter lumen 42 and the guidewire lumen 52. The guidewire 40 extends distally from the shaft distal end 26 and may be employed to assist in directing the shaft distal end 26 and balloon mounted occluding device 10 into a selected Fallopian tube. The guidewire 40 within the catheter lumen may extend through the mesh member 15, provided the guidewire 40 has a relatively small diameter compared with the mesh size. For example, a conventional guidewire 40 having a diameter of about 0.018 inch or less inch may typically be extended through the mesh member 15 without adversely affecting the mesh member 15.

The angled adapter 36 has an adapter lumen 46 that is coupled with a balloon inflation lumen 56 that extends the length of the catheter shaft 22 into the interior of the balloon 30 and is adapted to be coupled to an inflation medium source to selectively inflate and deflate the balloon 30.

The angled adapter 34 has an adapter lumen 44 that is coupled with a dye delivery lumen 54 that extends the length of the catheter shaft 22 to a plurality of dye ejection ports 50 proximal to the balloon 30. The dye delivery lumen 54 may comprise an annular or segmented outer lumen within outer sheath 38 and surrounding an inner sheath 48 enclosing the balloon inflation lumen 56 and the guidewire lumen 52. The dye ejection ports 50 may extend through and circumferentially around the outer sheath 38 and/or distal end of the dye delivery lumen may be left open rather than closed as depicted.

In use, the balloon 30 is inflated to expand the occluding member 10 against the Fallopian tube wall and deflated to retract the balloon from the occluding member lumen 14. Then, a bolus of tissue staining liquid dye of the types described above is that is coupled to adapter 34 is pumped through the adapter lumen 44 and the dye delivery lumen 54 and out of the dye ejection ports 50 to stain and visually mark the tissue at the Fallopian tube ostium.

In a second embodiment of an occluding device delivery catheter 60 of the present invention depicted in FIG. 6, a self-expanding occluding device 110 not necessarily having a marker 150 expands from a contracted outer diameter of FIGS. 1 and 2 to an expanded outer diameter of FIGS. 3 and 4 upon installation in a Fallopian tube by ejecting the contracted occluding device 110 from a distal cavity 78 of the delivery catheter shaft 62. In this embodiment, any configuration of mesh member 15 and/or barrier of the types described herein (not shown in FIG. 60 can be disposed within the occluding device lumen 114.

The exemplary delivery catheter 60 comprises an elongated catheter shaft 62 extending between a proximal end 68 connected with a proximal hub 64 to a distal end 66 distal to the deflated balloon 30. The proximal hub 64 comprises an axially and proximally extending adapter 72 and proximally extending angled adapter 74 that have adapter lumens 82 and 84, respectively, coupled to coaxial shaft lumens 92 and 94, respectively, within inner and outer sheathes 66 and 76, respectively, of catheter shaft 62.

The adapter lumen 82 of proximally extending adapter 72 is axially aligned with the push wire lumen 92 extending through the length of the shaft 62 to a push member 70 distal to push wire lumen 92 and abutting the occluding device proximal end 113 of occluding device 110 positioned in the distal cavity 78. It will be understood that the push wire 80 may extend distally of the distal cavity to provide a guiding function into a Fallopian tube.

In use, the proximal section of push wire 80 proximal to adapter 72 is pushed distally to apply force through push member 70 against the occluding member 110 to eject it distally out of the distal end opening of distal chamber 78 so that the occluding member 110 may be detached and self-expand in the Fallopian tube. Then, a bolus of tissue staining liquid dye of the types described above is that is coupled to adapter 74 is pumped through the adapter lumen 84 and the dye delivery lumen 94 and out of the dye ejection ports 90 to stain and visually mark the tissue at the Fallopian tube ostium. The dye ejection ports 90 may take any of the forms described above with respect to dye ejection ports 50.

Each delivery catheter 20, 60 bearing a contracted occluding device 10, 110 is preferably employed with a flexible hysteroscope of the type described in the above-referenced U.S. Patent Application Publication 2005/0288551 and depicted in part in FIGS. 7-13. Such a hysteroscope 100 comprises an elongated flexible and deflectable scope shaft 102 extending between a distal end 106 and a proximal end (not shown) disposed outside the patient's body and including distal end deflecting controls, a balloon inflation adapter, an illumination port, and an imaging port or adapter. In this preferred embodiment, an inflatable balloon 104 is supported on the shaft 102 to be inflated, via an inflation lumen of shaft 102, within the cervical canal or uterine cavity 114 of uterus 112 close to the cervix to seal the cervical canal and support scope shaft 102. A device delivery lumen is provided to receive and enable advancement of the occluding device delivery catheter 20, 60 therethrough in the steps of installing the occluding device 10, 110. Illumination and visualization components are included in the scope shaft 102 to enable illumination and visualization of the uterine cavity and right and left ostia of the right and left Fallopian tubes 116 and 118. A distal segment of the shaft 102 is deflectable through manipulation of deflection controls at the proximal end of the shaft 102 (not shown). The specific details of an exemplary hysteroscope to be employed in conjunction with the practice of the present invention are set forth in the above-referenced U.S. Patent Application Publication 2005/0288551.

Steps in the process of installing occluding devices 10, 10' in the right and left Fallopian tubes 116 and 118 employing the occluding device delivery catheter 20 are shown in FIGS. 7-12. A balloon inflation medium source 196, e.g., a syringe filled with fluid or gas, is coupled to the inflation adapter 36 to selectively inject or withdraw the inflation medium through the balloon inflation lumen 56 that extends the length of the catheter shaft 22 into the interior of the balloon 30 to inflate and deflate, respectively, the balloon 30. A dye source 194, e.g., a syringe filled with the selected dye, is coupled to the dye adapter 36 to selectively inject the dye through the dye delivery lumen 56 that extends the length of the catheter shaft 22 and out of the dye ejection ports 50 to mark the tissue of the ostium of the Fallopian tube that at least the first occluding device 10 is installed into.

Figure 7:
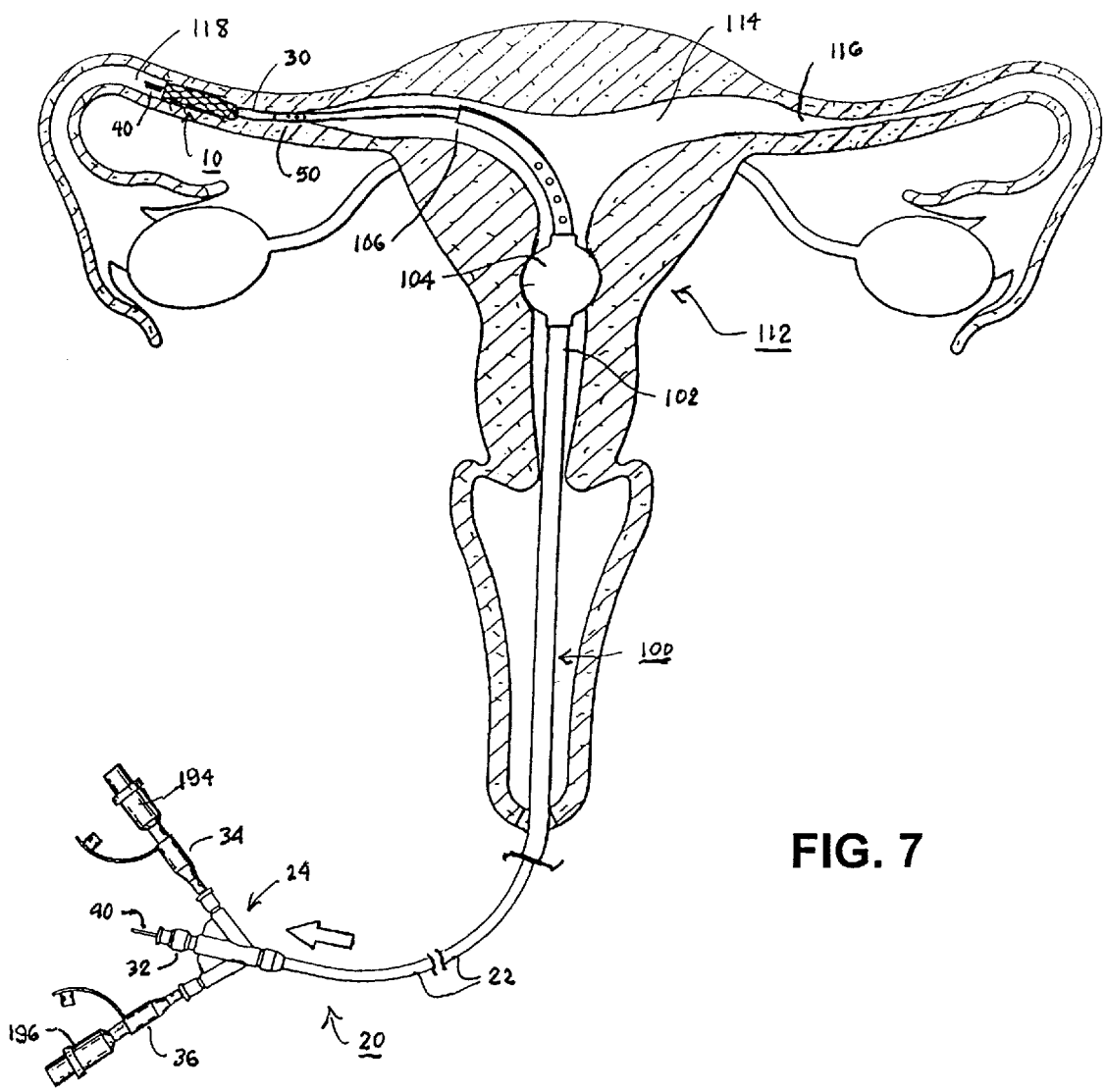
FIG. 7 is an illustration in partial cross-section depicting the transvaginal and transcervical advancement of a hysteroscope and the catheter shaft of the delivery catheter of FIG. 5 to install an occluding device in the left Fallopian tube.
Figure 8:
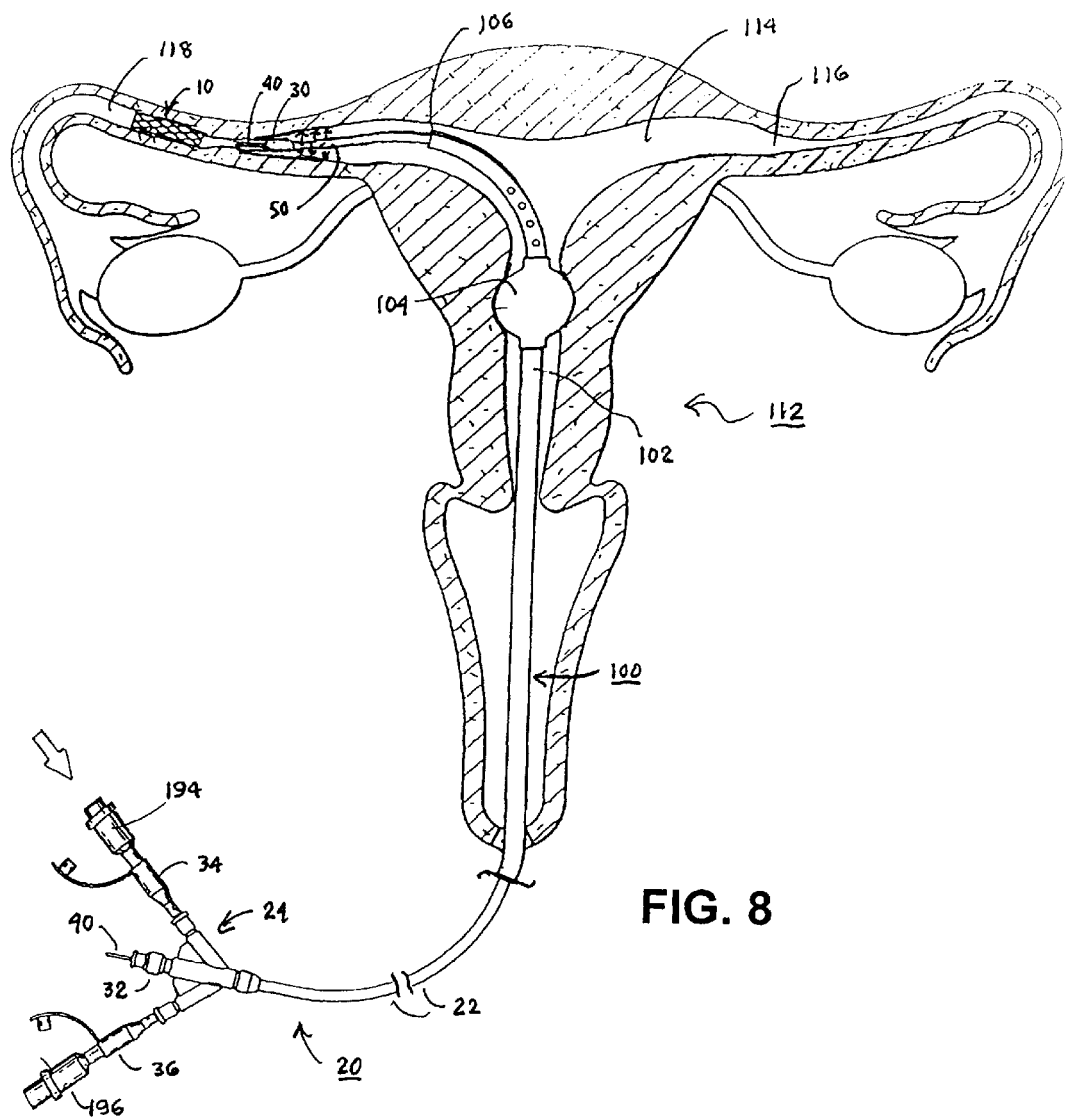
FIG. 8 is an illustration in partial cross-section depicting the retraction of the deflated balloon from the left Fallopian tube and the emission of dye from the dye emitting ports of the delivery catheter of FIG. 5 to visibly stain the ostium of the left Fallopian tube.
Figure 9:
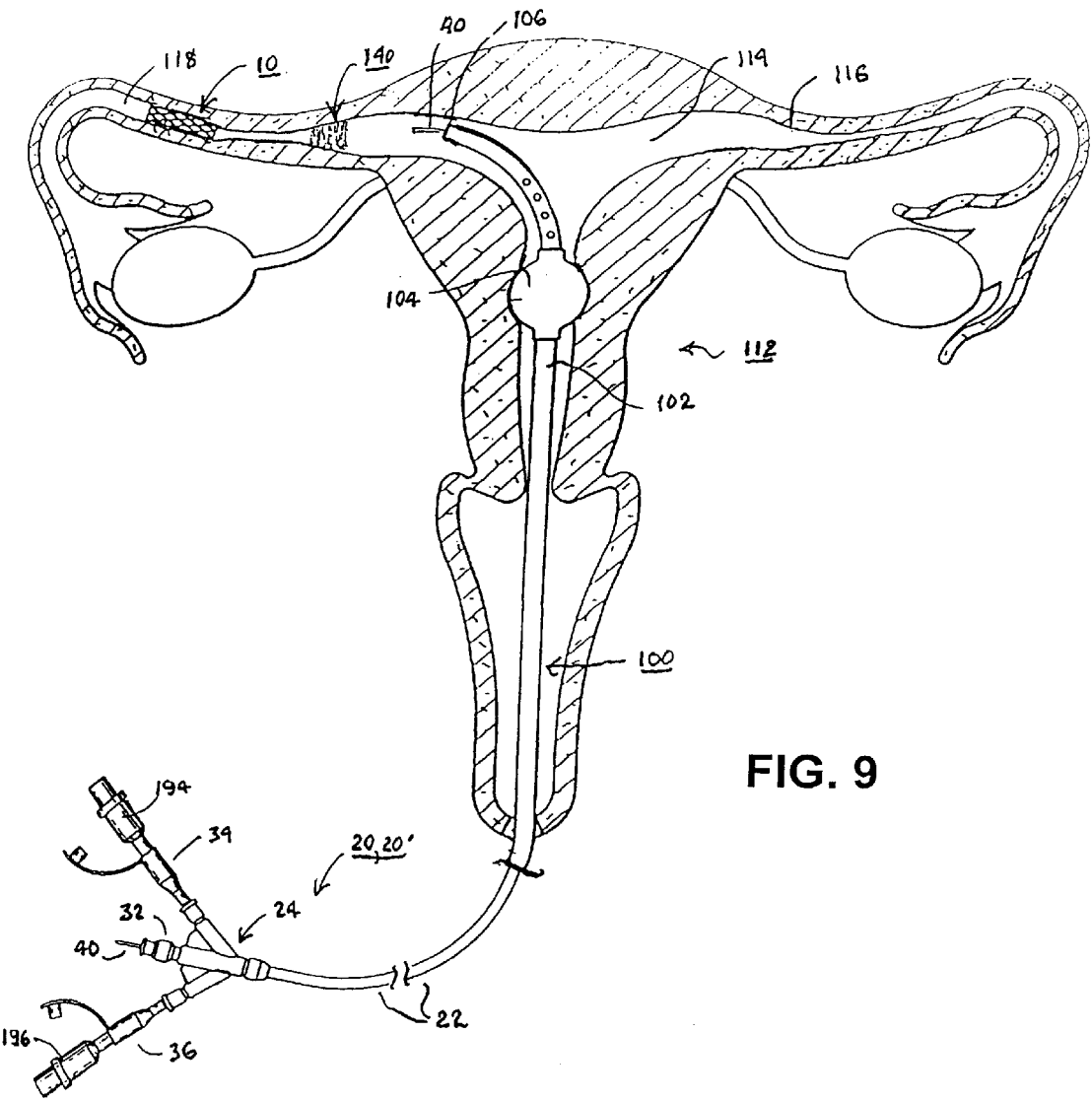
FIG. 9 is an illustration in partial cross-section depicting the viewing of the stain on the ostium of the left Fallopian tube employing the hysteroscope to aid in aiming the hysteroscope distal end away from the left Fallopian tube and toward the ostium of the right Fallopian tube for installation of a second occluding device employing the delivery catheter of FIG. 5 into it.
Figure 10:
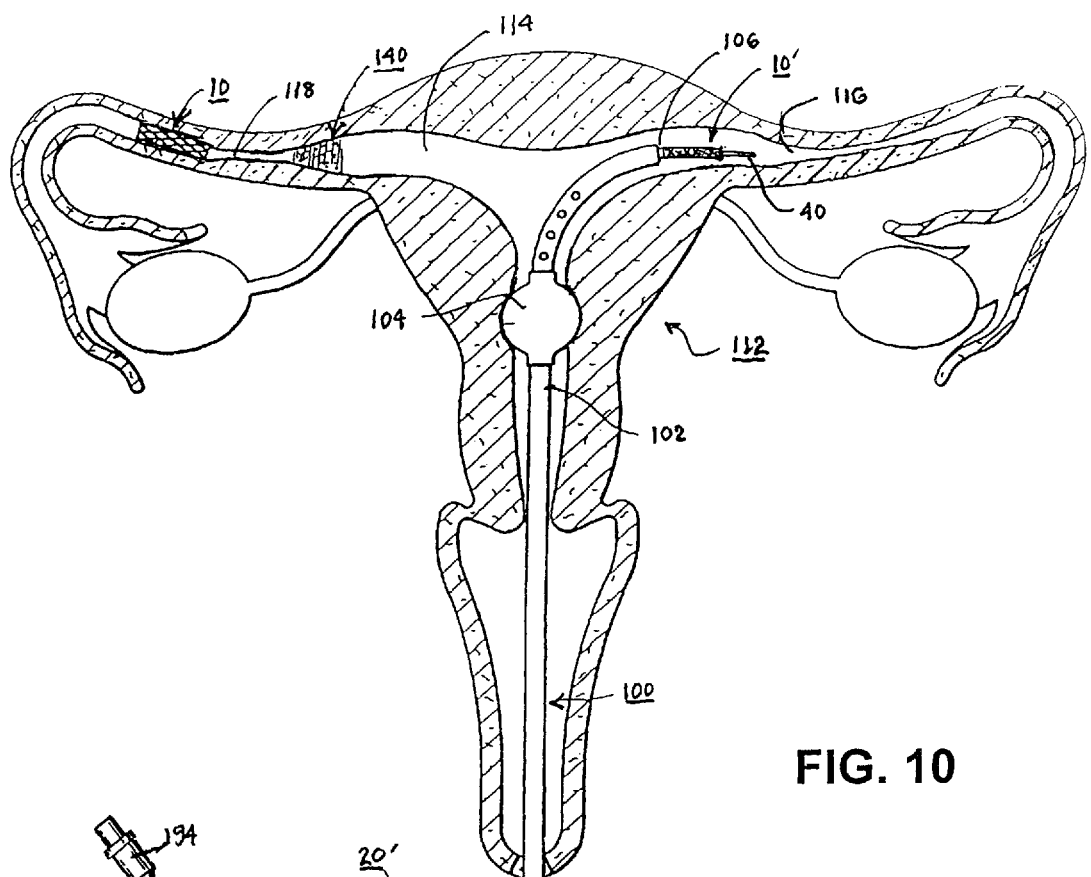
FIG. 10 is an illustration in partial cross-section depicting the aiming of the hysteroscope distal end toward and the advancement of the delivery catheter of FIG. 5 and a contracted second occluding device into the ostium of the right Fallopian tube in preparation for its installation in the right Fallopian tube.
Figure 10:
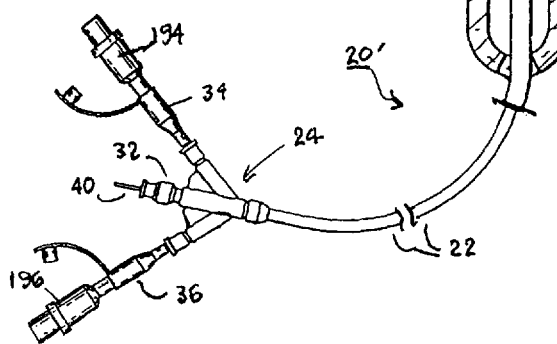

FIGS. 7-9 illustrate steps of installing the first occluding device 10 in the first Fallopian tube, in this instance the left Fallopian tube 118, and marking the first Fallopian tube ostium upon installation. In FIG. 7, the first occluding device 10 has been installed in the left Fallopian tube 118 by inflation of balloon 30 and the balloon 30 has been deflated. In FIG. 8, the bolus of dye is delivered by depressing a button of the dye source 194 to eject the through the dye delivery lumen 56 and out of the dye ejection ports 50 to mark the tissue of the ostium of the right Fallopian tube 118. The occluding device delivery catheter 20 may be retracted somewhat before or during marking. The resulting mark 140 is depicted in FIG. 9. The occluding device delivery catheter 20 is then withdrawn from the catheter lumen of the hysteroscope 100.

A second occluding device 10' may then be installed into the right Fallopian tube 116 employing the hysteroscope 100 with a second occluding device delivery catheter 20' of the same type as delivery catheter 20 or of another type. The installation of a second occluding device 10' of the same type as occluding device 10 loaded on the distal deflated balloon of the second occluding device delivery catheter 20' is illustrated in FIGS. 9-12. FIG. 9 also illustrates the initial step in the delivery of the second occluding device 20' into the right Fallopian tube 116, that is, observing which ostium is marked by the dye. The illumination and optical elements at the hysteroscope distal end 106 are directed toward the ostia of the right and left Fallopian tubes 116 and 118, and the hysteroscope distal end 106 is directed toward the ostium of the right Fallopian tube 116 in FIG. 10 after the mark 140 on the ostium of the left Fallopian tube 118 is observed in FIG. 9.

Figure 11:
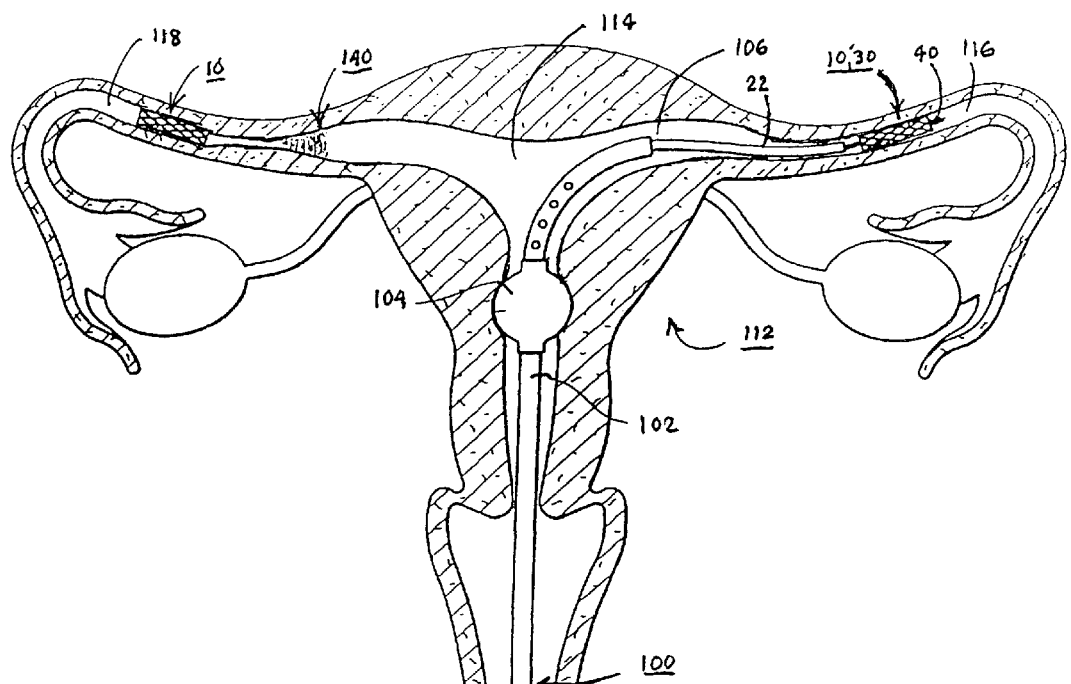
FIG. 11 is an illustration in partial cross-section depicting the expansion of the occluding device in the right Fallopian tube employing balloon of the delivery catheter of FIG. 5 advanced through a catheter lumen of the hysteroscope.
Figure 11:
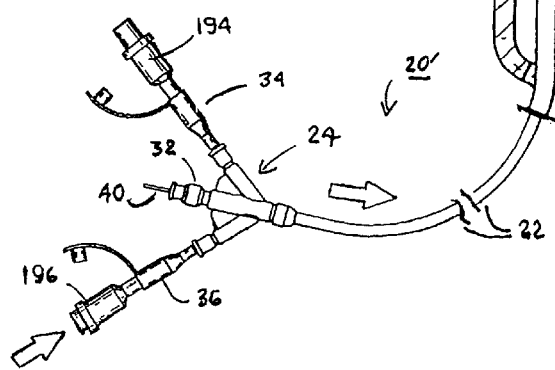
Figure 12:
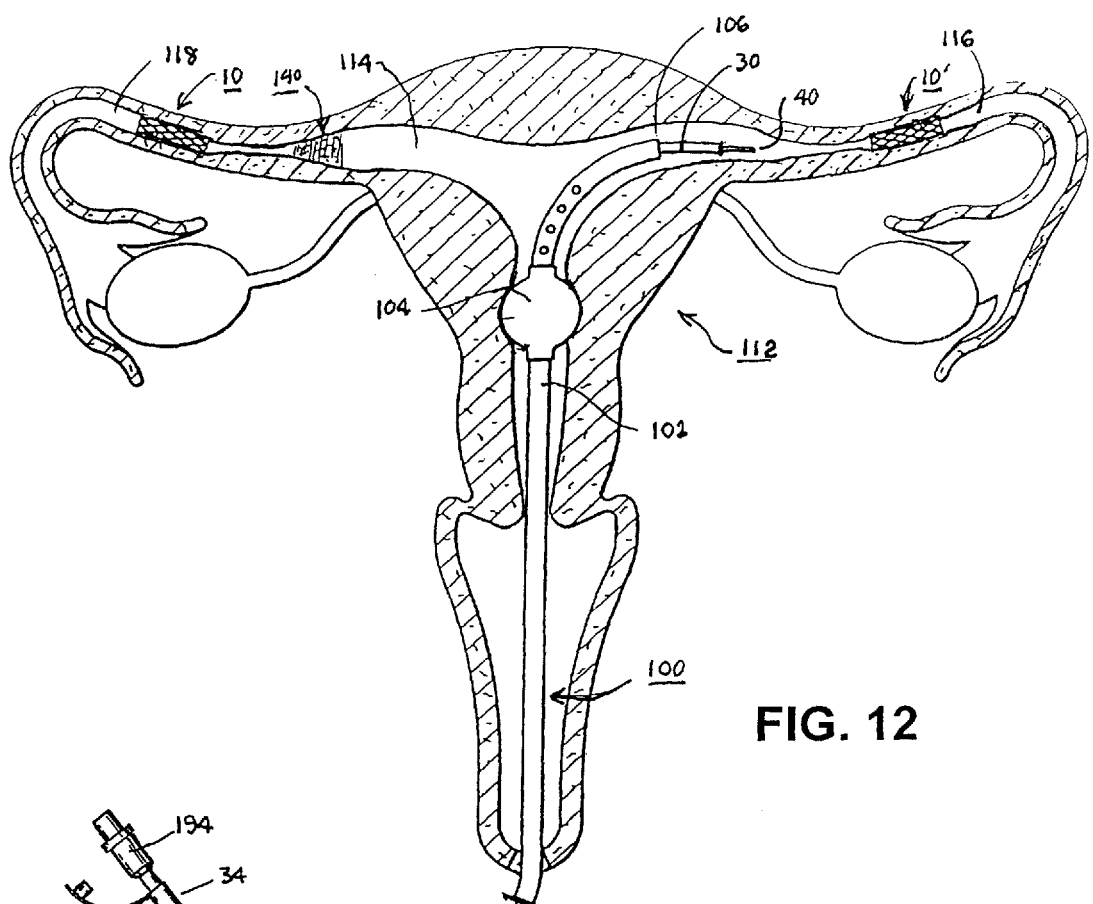
FIG. 12 is an illustration in partial cross-section depicting the retraction of the deflated balloon of the delivery catheter of FIG. 5 from the expanded occluding device lumen employing through the catheter lumen of the hysteroscope.
Figure 12:
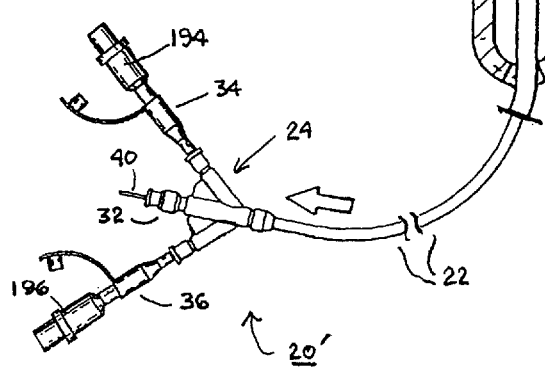

The subsequent steps of advancing the second occluding device 10' in the right Fallopian tube 116 and installing it by inflating balloon 30 by depressing the button of balloon inflation source 196 are depicted in FIG. 11. The deflation of balloon 30' and the retraction of the occluding device delivery catheter 20' is depicted in FIG. 12. Thus, in this exemplary method, only the left Fallopian tube 140 is marked to ensure that the second occluding device 10' is installed into the right Fallopian tube 116.

Figure 13:
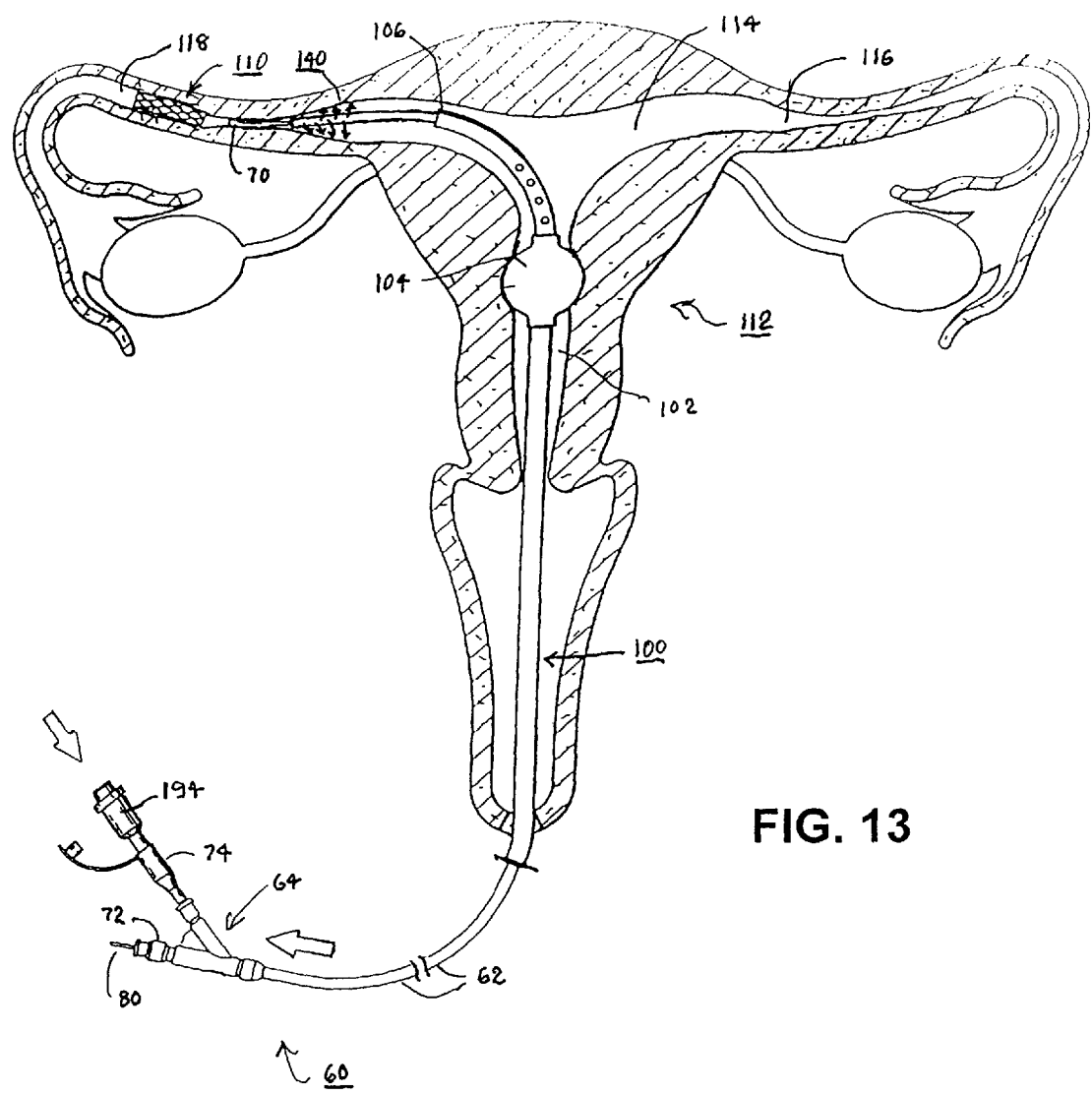
FIG. 13 is an illustration in partial cross-section depicting the retraction of the delivery catheter of FIG. 6 from the left Fallopian tube and the emission of dye from the dye emitting ports of the delivery catheter of FIG. 6 to visibly stain the ostium of the left Fallopian tube.

The steps of installing occluding devices 110 in the right and left Fallopian tubes 116 and 118 employing a pair of occluding device delivery catheters 60 of FIG. 6 are substantially the same as depicted in FIGS. 9-12. FIG. 13 depicts the step of ejecting the dye from the dye ejection ports 90 by depressing the button of dye source 194 to mark the ostium of the left Fallopian tube 118 with mark 140 following ejection and fixation of the self-expanding occluding device 110 within the left Fallopian tube. By observing the mark 140 as shown in FIG. 9 as described above, the right Fallopian tube ostium can be correctly identified in order to install the second occluding device 110 in the right Fallopian tube 116.

As described above, the dye stain that forms the mark 140 on the ostium of the Fallopian tube that the first occluding device 10, 110 is installed in can also be made in other ways not involving the ejection of dye through a dye lumen and out dye ejection ports proximate the delivery catheter distal end. In general, a selected dye of any of the types noted above is incorporated into a hydrophilic coating surface treatment on a member that contacts and stains the tissue of the tubal ostium when the distal portion of the occluding member catheter is extended into or withdrawn from the Fallopian tube. The member may comprise a part of the delivery catheter or a part of or extend proximally into the uterine cavity from the installed occluding device 10 or 110.

One embodiment involving a modification of the delivery catheter 20 and occluding device 10, for example, is depicted in FIGS. 14 and 15, wherein an elongated, preferably biodegradable, suture 150 is tied at tied end 154 to the outer member 11 near the occluding device proximal end 13. The suture 150 is surface coated or embedded with a hydrophilic composition including the selected dye to stain the ostium to form mark 140 or is simply colored with the selected non-toxic dye to be visible after installation employing the hysteroscope. For convenience of manufacturing and labeling, it may be desirable to provide both of the occluding device delivery catheters 120, 120' with respective occluding devices 10 and 10' each having a suture 150 tied thereto that extends into the uterine cavity upon installation of the occluding devices 10, 10'.

The occluding device delivery catheter 120, 120' is similar to occluding device 20 in that a distal balloon 130 is inflatable by an inflation medium pumped through an adapter lumen 146 in adapter 136 of hub 124 coupled to shaft proximal end 128, then through a balloon inflation lumen 156 in shaft 122, and then into the interior of balloon 130 in order to expand the occluding device 10, 10'. A guide wire 40 is extendable through the aligned guide wire lumens 142 and 152 of adapter 132 and shaft 122, respectively to extend through the device lumen 14 to and distally of the shaft distal end 126.

It will be understood that the suture 150 may be employed with the self-expanding occluding device 110, 110' as depicted in FIG. 6 by preferably tying the suture 150 at the device distal end 12 so that it extends distally out of the chamber 78 and proximally alongside the outer sheath 76 of the catheter shaft 62.

In either case, during the steps in the installation process entering the uterine cavity, the suture 150 trails proximally alongside the proximal portion of the deflated balloon 130 and along a distal section of the catheter shaft 122 or alongside the outer sheath 76 and within the catheter lumen of the hysteroscope. The suture 150 trails proximally as the occluding device 10, 10' or 110, 110' is ejected out of the hysteroscope lumen and directed toward a Fallopian tube ostium. The suture 150 trails proximally into the uterine cavity 114 when the occluding device 10, 10' or 110, 110' is advanced into and expanded within the Fallopian tube 116, 118. For example, the extension of the suture 150 from the occluding device 10 into the uterine cavity 114 following deflation and proximal withdrawal of the balloon 130 (or ejection of occluding device 110 from the chamber 76) is depicted in FIG. 15. Thus, the location of the first installed occluding device 10 (or 110) can be ascertained by visualizing the colored suture 150 within the uterine cavity 114 employing the optical system of the hysteroscope 100.

Figure 16:
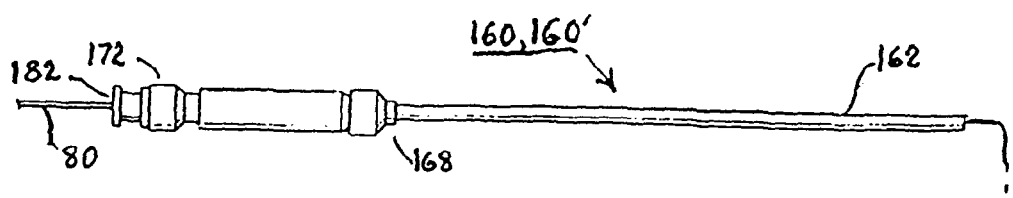
FIG. 16 is a side view in partial cross-section of the assembly of a contracted, self-expanding, occluding device mounted within a chamber at the distal end of a further embodiment of an occluding device delivery catheter adapted to mark the ostium that at least the first occluding device is installed into.
Figure 16:
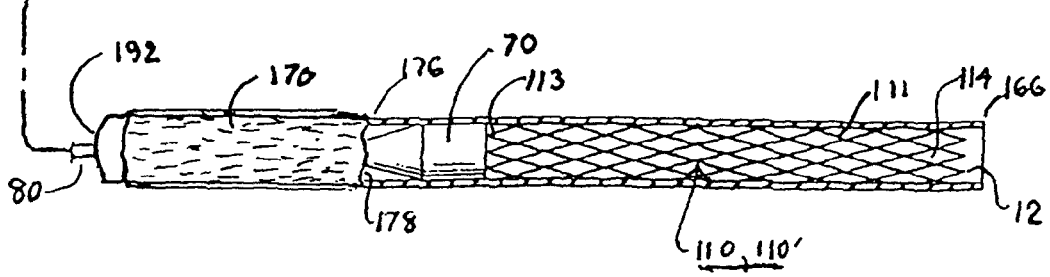

In another alternative embodiment depicted in FIG. 16, a selected dye of the types noted above is incorporated into a dye eluting or dye emitting body 170, e.g., a hydrophilic coating surface treatment along the distal occluding device delivery catheter shaft 162 of occluding device delivery catheter 160 or 160' in an application band extending partly or around the shaft 162. The dye emitting body 170 may extend proximally from the shaft distal end 166 or from a point proximal to the shaft distal end 166. For convenience of manufacturing and labeling, it may be desirable to provide both of the occluding device delivery catheters 160, 160' with a dye emitting body 170, since the marking of Fallopian tube ostium that the second delivered occluding device 110' is installed through is harmless.

The occluding device delivery catheter 160, 160' is similar to occluding device delivery catheter 60, 60' except that the features enabling dye delivery are also eliminated. Consequently, the hub 164 only comprises the push wire adapter 172 enclosing push wire lumen 182, and the shaft 162 only comprises the outer sheath 176 extending from shaft proximal end 168 coupled to hub 164 to shaft distal end 166, the outer sheath 176 enclosing a push wire lumen and the distal chamber 178. The push wire 80 extends through the aligned adapter lumen 182 and the shaft lumen to the push member 70 that bears against the occluding member proximal end 113.

In use of the occluding member delivery catheter 160 and 160', the installation of the occluding members 110 and 110' in the Fallopian tubes is simplified inasmuch as it is not necessary to employ a dye source and pump the dye through dye delivery lumens and out of distal dye emitting ports to stain the ostium of the first delivered occluding member 110. The dye in the dye emitting body 170 liquefies on contact with the ostium wall tissue to mark it as the occluding member 110, 110' is installed within a Fallopian tube.

It will be understood that the dye emitting body 170 may be employed in a modification of the delivery catheter 20 of FIG. 5 replacing the features providing marking through emission of dye staining the wall of the ostium of a Fallopian tube as described above. In such a modification, the dye emitting body 170 may be applied in a circumferential band to the outer surface of the catheter shaft 22 proximal to the balloon 30.

In still further embodiments of the invention, active or passive marking devices are provided at or near the catheter shaft distal end that are actively extended outward by manipulation of a proximal control mechanism or passively extend outward upon release from the catheter lumen of hysteroscope 100. For example, the dye emitting body may be applied to structures that extend outward of the catheter shaft when unrestrained and bend inward and proximally when restrained in the hysteroscope lumen.

Figure 17:
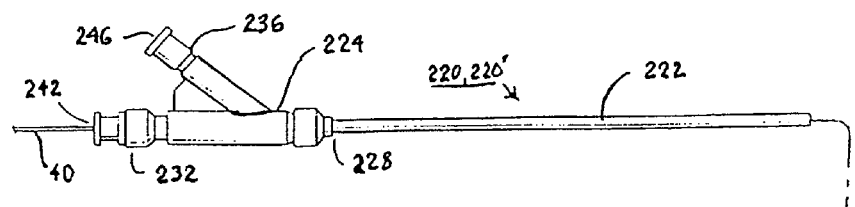
FIG. 17 is a side view in partial cross-section of the assembly of a contracted, balloon expandable, occluding device mounted upon an expandable balloon at the distal end of a further embodiment of an occluding device delivery catheter having outwardly extending brushes coated with a dye adapted to mark the ostium that at least the first occluding device is installed into.
Figure 18:
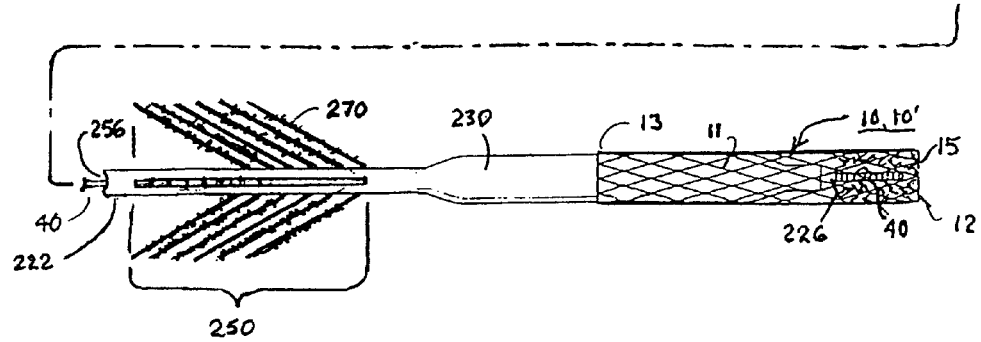
FIG. 18 is an expanded side view in partial cross-section of a distal end portion of the assembly of FIG. 17 showing the outwardly extending brushes confined within a hysteroscope lumen during introduction of the portion into the uterine cavity.
Figure 18:
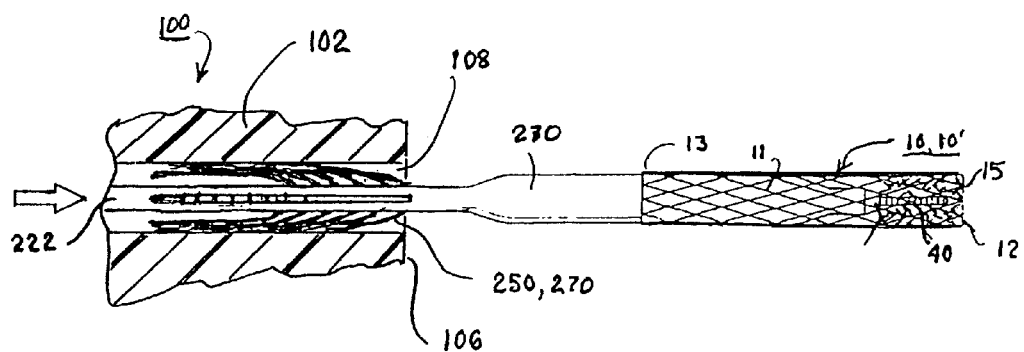
Figure 19:
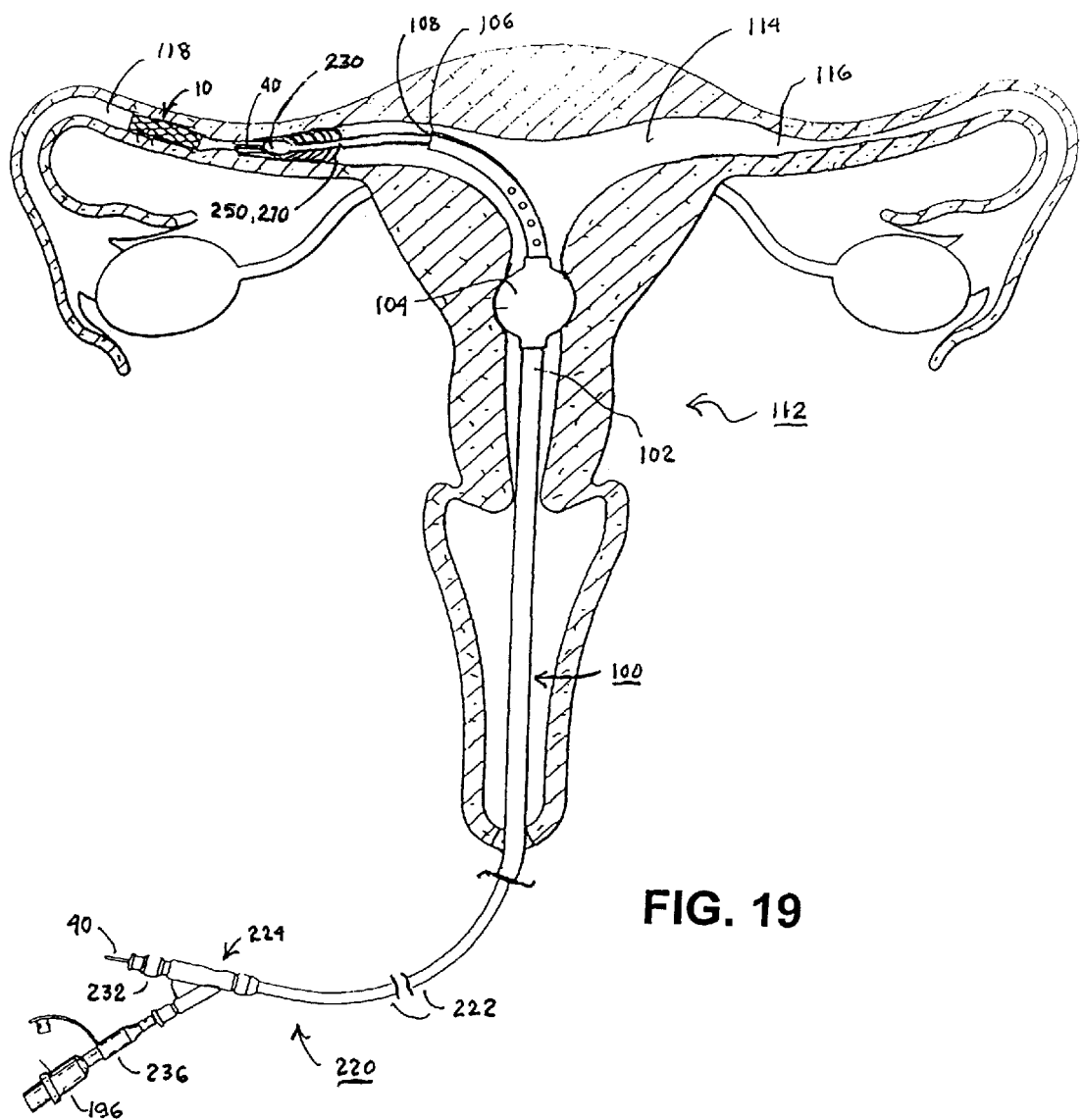
FIG. 19 is an illustration in partial cross-section depicting the retraction of the deflated balloon from the left Fallopian tube leaving the expanded occluding device in place and the brushing of dye from the dye bearing brushes onto the uterine wall to visibly stain the ostium of the left Fallopian tube.

An exemplary passive marker is depicted incorporated into the distal end section of the occluding device delivery catheter 220, 220' depicted in FIGS. 17-19. In this embodiment, the passive marker comprises an array of resilient fibers or flaps or brushes 250 coated with a hydrophilic compound and dye forming a dye emitting body 270. The resilient brushes 250 are radially disposed around the circumference of the catheter shaft 222 proximal to the occluding device expandable balloon 220 and extending outwardly and proximally. The resilient brushes 250 may extend at any selected angle to the axis of the shaft 222. The delivery catheter 220, 220' may otherwise take the form of and function as the delivery catheter 120, 120' of FIG. 14.

The resilient brushes 250 are bent against the shaft 222 and confined in the catheter lumen 108 of the hysteroscope 100 as shown in FIG. 18 during introduction into the uterine cavity 114. The brushes 250 spring back when released in the uterine cavity 114 and bear against the ostium wall as the contracted occluding device 10 and deflated balloon 230 are advanced into the left Fallopian tube 118. The occluding device 10 is expanded as the balloon 230 is expanded through depression of the button of inflation medium source 196 coupled to the inflation lumens of the adapter 236 and the shaft 222 in the manner as described above. The occluding device 10 is installed in the Fallopian tube 118 upon deflation of the balloon 230. Dye from the dye emitting body 270 borne by brushes 250 is transferred to the tissue wall while the occluding device 10 is being installed and continues to be transferred to stain the wall and provide the mark 140 as the brushes 250 are retracted as shown in FIG. 19 and until they are retracted into the catheter lumen 108.

As noted above, the brushes 250 may alternatively be actively extended outward from and retracted back into bores in the distal section of the shaft 222. One form of active extension may comprise provision of an inflatable balloon in the catheter shaft adjacent the brushes 250 that is selectively inflatable through a further inflation lumen to extend the brushes 250 outward. It will be understood that such active and passive fibers or flaps or brushes 250 bearing the dye emitting body 270 may be provided on occluding device delivery catheter 160, 160' of FIG. 16 in substitution for the dye emitting body 170.

In still further embodiments of the invention implemented for example in relation to the occluding devices 10, 10', for example, where guidewire 40 is employed in the process, the guidewire 40 may be coated with a hydrophilic dye containing compound, so that dye may stain the visible ostium of the Fallopian tube wall as the guidewire is first advanced through it and into the Fallopian tube. Thus, the marking step may be accomplished by such a guidewire alone or in conjunction with any of the other techniques disclosed herein.

Figure 20:
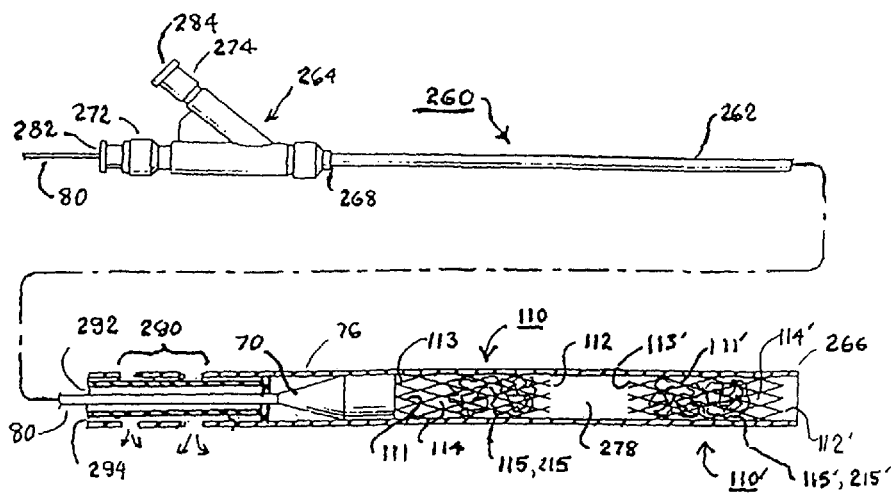
FIG. 20 is a side view in partial cross-section of the assembly of proximal and distal contracted, self-expanding, occluding devices mounted within a chamber at the distal end of a further embodiment of an occluding device delivery catheter adapted to mark the ostium that at least the first occluding device is installed into through liquefaction of dye coated occluding device inner member(s)
Figure 21:
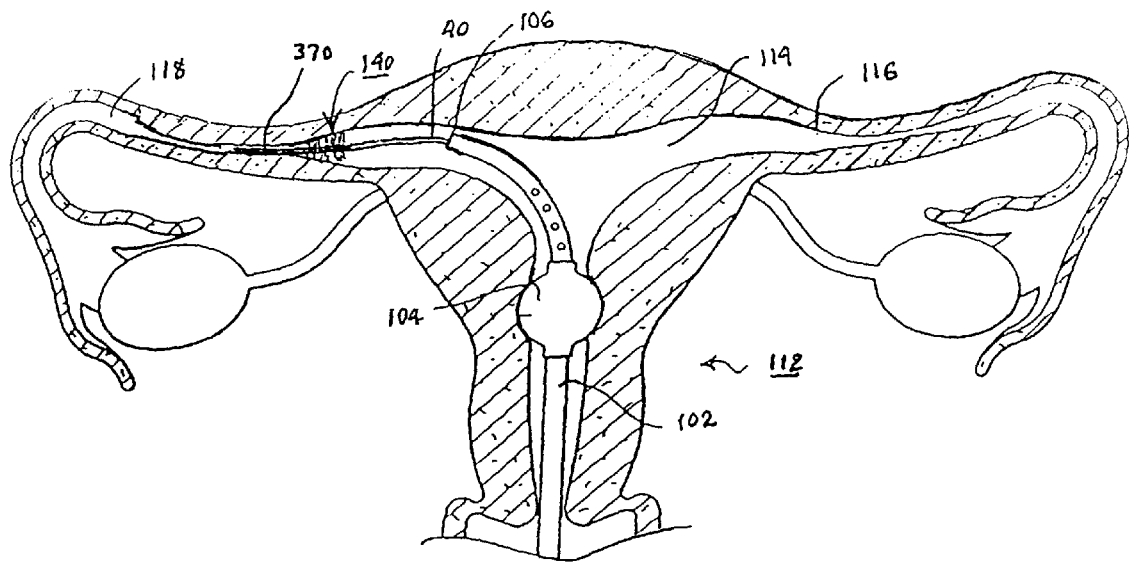
FIG. 21 is an illustration in partial cross-section depicting the transvaginal and transcervical advancement of a hysteroscope and guidewire bearing a dye emitting body into the left Fallopian tube and the formation of a mark of the ostium by emitted dye.

Still further embodiments of the invention are contemplated. The embodiments of the invention described above are implemented in two occluding device delivery catheters that are successively introduced and withdrawn from the catheter lumen of the hysteroscope 100 to dispose the first and second occluding devices in the first and second Fallopian tube and marking the ostium of at least the first Fallopian tube. It will be understood that the present invention may be implemented as disclosed in the above-referenced U.S. Patent Application Publication No. 2006/0009798 employing a single occluding device delivery catheter 260 as depicted in FIG. 20 having two relatively short occluding devices 110, 110' disposed end to end in the distal chamber 278 of the catheter shaft 262 to be successively installed in the first and second Fallopian tubes. When the catheter shaft distal end 266 is advanced into the first Fallopian tube, e.g., the left Fallopian tube, the push wire 80 is advanced to push the distal occluding device 110' out of the distal chamber 278 into the Fallopian tube to self-expand in situ.

Marking of the ostium of the first Fallopian tube may be accomplished in any of the above-described manners. For example, the occluding device delivery catheter 260 is configured in the same manner as the occluding device delivery catheter 60 of FIG. 6 having components enumerated to correspond to the enumerated components of FIG. 6, but prefixed with the number "2". The occluding device delivery catheter is therefore configured to deliver a tissue staining dye from distal ports 290 to form the mark 140 as depicted and described above with respect to FIGS. 7-13.

Then, the catheter shaft 266 can be directed under visualization through the ostium of the second Fallopian tube, and the proximal occluding device 110 may be ejected in the same fashion from the distal chamber 278 into the other Fallopian tube.

It is also contemplated that an alternative manner of staining the tissue to form mark 140 may be provided within occluding devices 10 and/or 10' and 110 and/or 110' in addition to or substitution for the above-described marking devices and methods. For example, the occluding devices 110, 110' depicted in FIG. 20 can be modified by encasing or coating at least the inner member 115' of the distal occluding device 110' with a hydrophilic dye containing compound to form a dye emitting body 215' that dissolves in the Fallopian tube when the distal occluding device 110' is installed. The ostium of the first Fallopian tube is stained to form mark 140 as the liquefied dye migrates along the tissue wall from the Fallopian tube lumen into the uterus.

The tubular members 111 and 111' depicted in FIG. 20 may also be coated with a dye-hydrophilic material mixture to form a dye emitting body. The tubular member 111, 111' may only be coated with a hydrophilic dye containing compound if an inner member 115, 115' is not disposed in the tubular member lumen. Both of the occluding devices 110 and 110' may be so modified to contain such a dye emitting body 215, 215' and/or be coated with the hydrophilic dye containing mixture for efficiency of manufacturing the occluding devices.

Thus, in this alternative embodiment also depicted in FIG. 20, the delivery catheter that is employed may be simplified by eliminating any other mechanisms for making the mark 140 including the depicted components 274, 284, 290 and 294.

In yet further embodiments of the invention wherein the occluding device delivery catheter is adapted to be advanced over a guide member, e.g., a stylet or guide wire or the like, it is contemplated that the visible marking of the tissue may be effected by providing a dye emitting body borne on at least a segment of the guide member proximate the guide member distal end adapted to contact and visibly stain the reproductive tract as the guide member is advanced into the reproductive tract. Thus, the distal segment of guidewire 40 may be coated with a dye emitting body 370. Dye from the dye emitting body 370 bearing against the ostium is transferred to the tissue to stain it and form the mark 140 while the guide wire 40 is advanced from the hysteroscope in the initial and final steps of installing the first occluding device in the first Fallopian tube 118. Thus, in this alternative embodiment also depicted in FIG. 20, the delivery catheter that is employed may be simplified by eliminating any other mechanisms for making the mark 140 including the depicted components 274, 284, 290 and 294.

All patents and publications referenced herein are hereby incorporated by reference in their entireties.

It will be understood that certain of the above-described structures, functions and operations of the above-described preferred embodiments are not necessary to practice the present invention and are included in the description simply for completeness of an exemplary embodiment or embodiments. It will also be understood that there may be other structures, functions and operations ancillary to the typical surgical procedures that are not disclosed and are not necessary to the practice of the present invention.

In addition, it will be understood that specifically described structures, functions and operations set forth in the above-referenced patents can be practiced in conjunction with the present invention, but they are not essential to its practice.

It is therefore to be understood, that within the scope of the appended claims, the invention may be practiced otherwise than as specifically described without actually departing from the spirit and scope of the present invention.

The invention claimed is:

1. A contraceptive system that effects occlusion of a reproductive tract comprising:
    an occluding device adapted to be installed within a reproductive tract lumen to occlude the reproductive tract lumen;
    means for installing the occluding device within said reproductive tract lumen; and
    a dye emitting body borne on an elongated flexible marker connected to the occluding device, wherein the elongated flexible marker trails proximally from the occluding device after the occluding device is installed within the reproductive tract lumen and the dye emitting body is adapted to emit a marking dye on contact with body tissue to form a mark on the body tissue adjacent said reproductive tract lumen to indicate installation of the occluding device within the reproductive tract lumen.

2. The contraceptive system of claim 1, the occluding device further comprising:

a tubular member having a first end, a second end, a member lumen extending therein, and an open-walled structure; and a tissue growth supporting member disposed within at least a section of the member lumen that encourages or supports tissue growth to thereby chronically occlude the reproductive body lumen.

3. The contraceptive system of claim 2, wherein the tubular member is compressible and expandable when disposed within the reproductive tract; and the means for installing further comprises an elongated occluding device delivery catheter having a catheter shaft extending between a proximal end and a distal end, the catheter further comprising: an expandable member at the shaft distal end supporting the occluding device during introduction into the reproductive tract; means for expanding the expandable member to expand the occluding device within the reproductive tract; and means for contracting the expandable member to enable withdrawal of the catheter.

4. The contraceptive system of claim 2, wherein the tubular member is selectively expandable within the reproductive tract by the means for installing; and the means for installing further comprises means for expanding the tubular member within the reproductive tract to engage with the reproductive tract tissue lining.

5. The contraceptive system of claim 1 wherein the elongated flexible marker comprises a suture connected to the occluding device.

6. The contraceptive system of claim 1, wherein the means for installing the occluding device comprises:

an elongated occluding device delivery catheter having a catheter shaft extending between a shaft proximal end and a shaft distal end; and a push member within the catheter shaft to apply force against the occluding device and eject the occluding device distally out of the catheter shaft.

7. The contraceptive system of claim 6, wherein the occluding device self-expands to engage with tissue lining of the reproductive tract lumen when ejected from the distal chamber.

8. The contraceptive system of claim 1, wherein the dye emitting body comprises a hydrophilic material and a dye.

9. The contraceptive system of claim 8, wherein the hydrophilic material liquefies when in contact with the body tissue or body fluid.

10. The contraceptive system of claim 1, wherein the dye emitting body comprises a bioabsorbable material and a dye.

11. The contraceptive system of claim 1, wherein the occluding device further comprises a tubular member having a first end, a second end and a member lumen extending therein.

12. The contraceptive system of claim 11 wherein the means for installing the occluding device comprises:

an elongated occluding device delivery catheter having a catheter shaft extending between a shaft proximal end and a shaft distal end;

a balloon inflation lumen extending substantially between the shaft proximal end and an expandable balloon within the member lumen; and means for selectively delivering a balloon inflating fluid through the balloon inflation lumen and into the balloon to expand the balloon against the tubular member to effect the expansion of the tubular member within the reproductive tract and for withdrawing the balloon inflating fluid to deflate the balloon and enable retraction of the catheter from the reproductive tract.

13. The contraceptive system of claim 1, wherein the reproductive tract lumen is a Fallopian tube, and the elongated flexible marker extends into a uterine cavity to mark the Fallopian tube after the occluding device is installed within the Fallopian tube.

14. The contraceptive system of claim 1, wherein the elongated flexible marker is adapted to extend from the reproductive tract lumen following installation of the occluding device therein.

15. The contraceptive system of claim 1, wherein the dye emitting body is adapted to form a visible stain on the tissue of an ostium or uterine cavity.

16. The contraceptive system of claim 1, wherein the dye emitting body borne on the elongated flexible marker is adapted to extend into a uterine cavity after the occluding device is installed within the reproductive tract lumen.

17. The contraceptive system of claim 1, wherein the elongated flexible marker is attached to the occluding device near a proximal end of the occluding device.

18. The contraceptive system of claim 1, wherein the dye emitting body is biodegradable over time.

19. The contraceptive system of claim 1, wherein the elongated flexible marker is attached to the occluding device near a distal end of the occluding device.

20. A contraceptive system that effects occlusion of a reproductive tract comprising:

an occluding device adapted to be installed within a reproductive tract lumen to occlude the reproductive tract lumen;

an elongated occluding device delivery catheter having a catheter shaft enclosing a shaft lumen and extending between a shaft proximal end and a shaft distal end, the shaft lumen terminating in a distal chamber at the shaft distal end, wherein the occluding device is disposed within the distal chamber;

a push member within the catheter shaft to apply force against the occluding device and eject the occluding device distally out of the distal chamber; and a dye emitting body borne on the occluding device, the dye emitting body adapted to emit a marking dye on contact with body tissue to form a mark on the body tissue adjacent said reproductive tract lumen to indicate installation of the occluding device within the reproductive tract lumen.

21. The contraceptive system of claim 20, further comprising a second occluding device disposed within the distal chamber.

22. A contraceptive system that effects occlusion of a reproductive tract comprising:

an occluding device adapted to be installed within a reproductive tract lumen to occlude the reproductive tract lumen;

an elongated occluding device delivery catheter having a catheter shaft enclosing a shaft lumen and extending between a shaft proximal end and a shaft distal end, the shaft lumen terminating in a distal chamber at the shaft distal end, wherein the occluding device is disposed in the distal chamber;

a push member within the catheter shaft to apply force against the occluding device and eject the occluding device distally out of the distal chamber; and a dye emitting composition borne on an elongated flexible marker connected to the occluding device, wherein the elongated flexible marker trails proximally from the occluding device after the occluding device is installed within the reproductive tract lumen and the dye emitting body is adapted to emit a marking dye on contact with body tissue to form a mark on the body tissue adjacent said reproductive tract lumen to indicate installation of the occluding device within the reproductive tract lumen.

23. The contraceptive system of claim 22, wherein the dye emitting composition is a coating on the elongated flexible marker.

24. The contraceptive system of claim 22, wherein the elongated flexible marker is embedded with the dye emitting composition.

25. The contraceptive system of claim 22, wherein the reproductive tract lumen is a Fallopian tube, and the elongated flexible marker is adapted to extend into a uterine cavity after the occluding device is installed within the Fallopian tube.

26. The contraceptive system of claim 22, wherein the dye emitting body comprises a hydrophilic material and a dye.

27. The contraceptive system of claim 22, wherein the dye emitting body comprises a bioabsorbable material and a dye.

28. The contraceptive system of claim 22, wherein the elongated flexible marker is biodegradable.

29. The contraceptive system of claim 22, wherein the occluding device self-expands to engage with tissue lining of the reproductive tract lumen when ejected from the distal chamber.

30. A contraceptive system that effects occlusion of a reproductive tract comprising:

an occluding device adapted to installed within a reproductive tract lumen to occlude the reproductive tract lumen, the occluding device comprising:

a tubular member having a first end, a second end, a member lumen extending therein, and an open-walled structure; and a tissue growth supporting member disposed within at least a section of the member lumen that encourages or supports tissue growth to thereby chronically occlude the reproductive body lumen;

means for installing the occluding device within said reproductive tract lumen; and a dye emitting body borne on the tissue growth supporting member, the dye emitting body adapted to emit a marking dye on contact with body tissue to form a mark on the body tissue adjacent said reproductive tract lumen to indicate installation of the occluding device within the reproductive tract lumen.

\* \* \* \* \*